(12) United States Patent
Shim et al.

(10) Patent No.: US 10,732,574 B2
(45) Date of Patent: Aug. 4, 2020

(54) WATCH TYPE TERMINAL AND METHOD FOR CONTROLLING THE SAME

(71) Applicant: LG ELECTRONICS INC., Seoul (KR)

(72) Inventors: Hongjo Shim, Seoul (KR); Hyunok Lee, Seoul (KR); Mihyun Park, Seoul (KR); Jeonghan Kim, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 870 days.

(21) Appl. No.: 15/299,378

(22) Filed: Oct. 20, 2016

(65) Prior Publication Data

US 2017/0315511 A1 Nov. 2, 2017

Related U.S. Application Data

(60) Provisional application No. 62/328,624, filed on Apr. 28, 2016.

(30) Foreign Application Priority Data

Jun. 10, 2016 (KR) .................. 10-2016-0072689

(51) Int. Cl.
*G04B 47/06* (2006.01)
*A61B 5/00* (2006.01)
(Continued)

(52) U.S. Cl.
CPC ........ *G04B 47/063* (2013.01); *A61B 5/02427* (2013.01); *A61B 5/02438* (2013.01);
(Continued)

(58) Field of Classification Search
CPC .............. A61B 5/1455; A61B 5/14551; A61B 5/14552; A61B 5/6824
See application file for complete search history.

(56) References Cited

U.S. PATENT DOCUMENTS

| 6,330,468 B1 | 12/2001 | Scharf |
| 2014/0275854 A1 | 9/2014 | Venkatraman et al. |
| 2015/0355604 A1 | 12/2015 | Fraser et al. |

FOREIGN PATENT DOCUMENTS

| CN | 102885613 | 1/2013 |
| WO | 9822018 | 5/1998 |
| WO | 2015084375 | 6/2015 |

OTHER PUBLICATIONS

European Patent Office Application Serial No. 16194757.7, Search Report dated May 23, 2017, 8 pages.

(Continued)

*Primary Examiner* — Eric F Winakur
(74) *Attorney, Agent, or Firm* — Lee, Hong, Degerman, Kang & Waimey

(57) ABSTRACT

The present invention relates to a watch type terminal, including a main body, and a sensing unit disposed on one surface of the main body and configured to acquire a biometric signal, wherein the sensing unit includes at least one green light emitting device provided on one surface of the main body and configured to output green light, at least one yellow light emitting device disposed with being spaced apart from the at least one green light emitting device, and configured to output yellow light with a different skin transmittance from that of the green light, a light receiving sensor surrounded by the green light emitting device and the yellow light emitting device, and configured to receive reflected green light and/or yellow light, and a controller configured to generate a biometric signal using light incident on the light receiving sensor.

18 Claims, 36 Drawing Sheets

(51) Int. Cl.
  *A61B 5/1455* (2006.01)
  *A61B 5/024* (2006.01)
  *A61B 5/145* (2006.01)
  *G01N 21/35* (2014.01)

(52) U.S. Cl.
  CPC ........ *A61B 5/1455* (2013.01); *A61B 5/14542* (2013.01); *A61B 5/14551* (2013.01); *A61B 5/681* (2013.01); *A61B 5/6824* (2013.01); *A61B 5/6843* (2013.01); *A61B 5/721* (2013.01); *A61B 5/7221* (2013.01); *A61B 5/7278* (2013.01); *A61B 5/742* (2013.01); *G01N 21/35* (2013.01); *A61B 2562/046* (2013.01); *A61B 2562/185* (2013.01)

(56) References Cited

OTHER PUBLICATIONS

State Intellectual Property Office of the People's Republic of China Application Serial No. 201611202934.9, Office Action dated Mar. 8, 2019, 14 pages.

Xinrong, L., "Head and neck hemangioma and vascular malformation," Science and Technology Literature Publishing House, Feb. 2010, pp. 57, 5 pages.

State Intellectual Property Office of the People's Republic of China Application Serial Number 201611202934.9, Decision of Rejection dated Mar. 19, 2020, 8 pages.

Xie, Z. et al., "Electronic circuit design, experiment, test, Second edition" Huazhong University of Technology Press, Jul. 2000, 12 pages.

Yang, X. et al., "The basis and practice of electronic design competition," Hefei University of Technology Press, Jul. 2012, 7 pages.

Hu, R. et al., "Selection of electrical and electronic experiment cases," Beijing University of Posts and Telecommunications Press, Apr. 2015, 10 pages.

WATCH TYPE TERMINAL AND METHOD FOR CONTROLLING THE SAME

CROSS-REFERENCE TO RELATED APPLICATION

Pursuant to 35 U.S.C. § 119, this application claims the benefit of earlier filing date and right of priority to Korean Application No. 10-2016-0072689, filed on Jun. 10, 2016, and also claims the benefit of U.S. Provisional Application No. 62/328,624, filed on Apr. 28, 2016, the contents of each are all hereby incorporated by reference herein in their entireties.

BACKGROUND OF THE INVENTION

1. Field of the Invention

This specification relates to a mobile terminal having a sensor capable of detecting (measuring) a biometric signal, and a method for controlling the same.

2. Background of the Invention

Terminals may be divided into glass type terminals (mobile/portable terminals) and stationary terminals according to their mobility. Also, the glass type terminals may be classified into handheld terminals and vehicle mount terminals according to whether or not a user can directly carry.

As it becomes multifunctional, a mobile terminal can be allowed to capture still images or moving images, play music or video files, play games, receive broadcast and the like, so as to be implemented as an integrated multimedia player. Many efforts include not only changes and improvement of structural components implementing a mobile terminal but also software improvement to support and improve functions of the terminal.

With development of wearable terminals worn on a part of a user's body, various sensing units for collecting biometric signals using the wearable terminals are studied. However, the collection or measurement of the biometric signals using the wearable terminal is difficult due to a small size of the wearable terminal, frequent movements of the wearable terminal in a worn state on the body, and a characteristic of a worn area of the body.

SUMMARY OF THE INVENTION

Therefore, an aspect of the detailed description is to provide a watch type terminal having a sensing unit, which is provided with a light receiving sensor and a light emitting device spaced apart from each other by a specific distance for measuring an accurate biometric signal.

To achieve these and other advantages and in accordance with the purpose of this specification, as embodied and broadly described herein, there is provided a watch type terminal, including a main body, and a sensing unit disposed on one surface of the main body and configured to acquire a biometric signal, wherein the sensing unit includes at least one green light emitting device provided on one surface of the main body and configured to output green light, at least one yellow light emitting device disposed with being spaced apart from the at least one green light emitting device, and configured to output yellow light with a different skin transmittance from that of the green light, a light receiving sensor surrounded by the green light emitting device and the yellow light emitting device, and configured to receive reflected green light and/or yellow light, and a controller configured to generate a biometric signal using light incident on the light receiving sensor.

In accordance with one embodiment of the present invention, when a biometric signal acquired using green light is in an abnormal range, biometric signals can be measured by outputting yellow light, whereby more accurate biometric signals can be acquired according to skin colors and skin thickness.

In accordance with one embodiment of the present invention, a light emitting device and a light receiving sensor can be individually disposed on one area of a watch type terminal, and accordingly, a red light emitting device outputting red light can be disposed with being spaced apart from the light emitting device and/or the light receiving sensor, thereby measuring oxygen saturation.

In accordance with one embodiment of the present invention, individually arranged light emitting device and light receiving sensor may be spaced with an interval capable of optimizing performances, and a light shielding structure of preventing a leakage of light and an introduction of unnecessary light can be employed, thereby enhancing sensing efficiency.

Also, oxygen saturation can be measured by additionally arranging a red light emitting device spaced apart from a light receiving sensor by more than a specific distance, thereby collecting more accurate biometric signals.

A more accurate measurement can be performed according to a color or thickness of a skin by arranging different types of devices of outputting green light and yellow light.

Further scope of applicability of the present application will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from the detailed description.

BRIEF DESCRIPTION OF THE DRAWINGS

The accompanying drawings, which are included to provide a further understanding of the invention and are incorporated in and constitute a part of this specification, illustrate exemplary embodiments and together with the description serve to explain the principles of the invention.

In the drawings.

DETAILED DESCRIPTION OF THE INVENTION

Figure 1A:
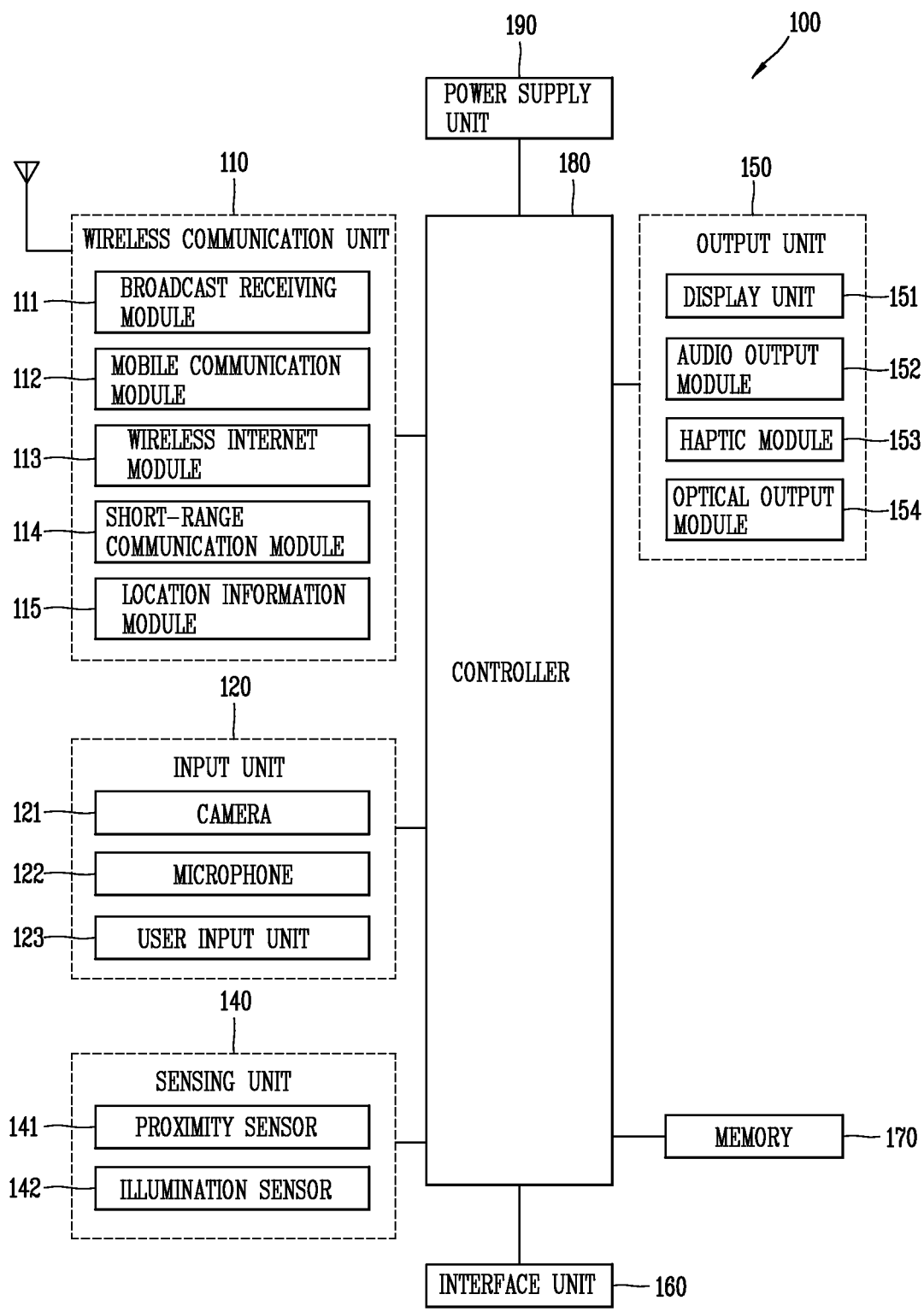
FIG. 1A is a block diagram of a watch type terminal in accordance with one exemplary embodiment of the present invention.

Description will now be given in detail according to exemplary embodiments disclosed herein, with reference to the accompanying drawings. For the sake of brief description with reference to the drawings, the same or equivalent components may be provided with the same or similar reference numbers, and description thereof will not be repeated. In general, a suffix such as "module" and "unit" may be used to refer to elements or components. Use of such a suffix herein is merely intended to facilitate description of the specification, and the suffix itself is not intended to give any special meaning or function. In the present disclosure, that which is well-known to one of ordinary skill in the relevant art has generally been omitted for the sake of brevity. The accompanying drawings are used to help easily understand various technical features and it should be understood that the embodiments presented herein are not limited by the accompanying drawings. As such, the present disclosure should be construed to extend to any alterations, equivalents and substitutes in addition to those which are particularly set out in the accompanying drawings.

It will be understood that although the terms first, second, etc. may be used herein to describe various elements, these elements should not be limited by these terms. These terms are generally only used to distinguish one element from another.

It will be understood that when an element is referred to as being "connected with" another element, the element can be connected with the other element or intervening elements may also be present. In contrast, when an element is referred to as being "directly connected with" another element, there are no intervening elements present.

A singular representation may include a plural representation unless it represents a definitely different meaning from the context.

Terms such as "include" or "has" are used herein and should be understood that they are intended to indicate an existence of features, numbers, steps, functions, several components, or combinations thereof, disclosed in the specification, and it is also understood that greater or fewer features, numbers, steps, functions, several components, or combinations thereof may likewise be utilized.

Mobile terminals presented herein may be implemented using a variety of different types of terminals. Examples of such terminals include cellular phones, smart phones, user equipment, laptop computers, digital broadcast terminals, personal digital assistants (PDAs), portable multimedia players (PMPs), navigators, slate PCs, tablet PCs, ultra books, wearable devices (for example, smart watches, smart glasses, head mounted displays (HMDs)), and the like.

By way of non-limiting example only, further description will be made with reference to particular types of mobile terminals. However, such teachings apply equally to other types of terminals, such as those types noted above. In addition, these teachings may also be applied to stationary terminals such as digital TV, desktop computers, digital signage, and the like.

FIG. 1A is a block diagram of a mobile terminal in accordance with the present invention.

The mobile terminal 100 is shown having components such as a wireless communication unit 110, an input unit 120, a sensing unit 140, an output unit 150, an interface unit 160, a memory 170, a controller 180, and a power supply unit 190. It is understood that implementing all of the illustrated components is not a requirement, and that greater or fewer components may alternatively be implemented.

In more detail, the wireless communication unit 110 typically includes one or more modules which permit communications such as wireless communications between the mobile terminal 100 and a wireless communication system, communications between the mobile terminal 100 and another mobile terminal, communications between the mobile terminal 100 and an external server. Further, the wireless communication unit 110 typically includes one or more modules which connect the mobile terminal 100 to one or more networks.

The wireless communication unit 110 includes one or more of a broadcast receiving module 111, a mobile communication module 112, a wireless Internet module 113, a short-range communication module 114, and a location information module 115.

The input unit 120 includes a camera 121 or an image input unit for obtaining images or video, a microphone 122, which is one type of audio input device for inputting an audio signal, and a user input unit 123 (for example, a touch key, a mechanical key, and the like) for allowing a user to input information. Data (for example, audio, video, image, and the like) is obtained by the input unit 120 and may be analyzed and processed according to user commands.

The sensing unit 140 is typically implemented using one or more sensors configured to sense internal information of the mobile terminal, the surrounding environment of the mobile terminal, user information, and the like. For example, the sensing unit 140 may include at least one of a proximity sensor 141, an illumination sensor 142, a touch sensor, an acceleration sensor, a magnetic sensor, a G-sensor, a gyroscope sensor, a motion sensor, an RGB sensor, an infrared (IR) sensor, a finger scan sensor, a ultrasonic sensor, an optical sensor (for example, camera 121), a microphone 122, a battery gauge, an environment sensor (for example, a barometer, a hygrometer, a thermometer, a radiation detection sensor, a thermal sensor, and a gas sensor, among others), and a chemical sensor (for example, an electronic nose, a health care sensor, a biometric sensor, and the like). The mobile terminal disclosed herein may be configured to utilize information obtained from one or more sensors of the sensing unit 140, and combinations thereof.

The output unit 150 is typically configured to output various types of information, such as audio, video, tactile output, and the like. The output unit 150 is shown having at least one of a display unit 151, an audio output module 152, a haptic module 153, and an optical output module 154. The display unit 151 may have an inter-layered structure or an integrated structure with a touch sensor in order to facilitate a touch screen. The touch screen may provide an output interface between the mobile terminal 100 and a user, as well as function as the user input unit 123 which provides an input interface between the mobile terminal 100 and the user.

The interface unit 160 serves as an interface with various types of external devices that can be coupled to the mobile terminal 100. The interface unit 160, for example, may include any of wired or wireless ports, external power supply ports, wired or wireless data ports, memory card ports, ports for connecting a device having an identification module, audio input/output (I/O) ports, video I/O ports, earphone ports, and the like. In some cases, the mobile terminal 100 may perform assorted control functions associated with a connected external device, in response to the external device being connected to the interface unit 160.

The memory 170 is typically implemented to store data to support various functions or features of the mobile terminal 100. For instance, the memory 170 may be configured to store application programs executed in the mobile terminal 100, data or instructions for operations of the mobile terminal 100, and the like. Some of these application programs may be downloaded from an external server via wireless communication. Other application programs may be installed within the mobile terminal 100 at time of manufacturing or shipping, which is typically the case for basic functions of the mobile terminal 100 (for example, receiving a call, placing a call, receiving a message, sending a message, and the like). It is common for application programs to be stored in the memory 170, installed in the mobile terminal 100, and executed by the controller 180 to perform an operation (or function) for the mobile terminal 100.

The controller 180 typically functions to control overall operation of the mobile terminal 100, in addition to the operations associated with the application programs. The controller 180 may provide or process information or functions appropriate for a user by processing signals, data, information and the like, which are input or output by the aforementioned various components, or activating application programs stored in the memory 170.

Also, the controller 180 controls some or all of the components illustrated in FIG. 1A according to the execution of an application program that have been stored in the memory 170. In addition, the controller 180 may control at least two of those components included in the mobile terminal to activate the application program.

The power supply unit 190 can be configured to receive external power or provide internal power in order to supply appropriate power required for operating elements and components included in the mobile terminal 100. The power supply unit 190 may include a battery, and the battery may be configured to be embedded in the terminal body, or configured to be detachable from the terminal body.

At least part of the components may cooperatively operate to implement an operation, a control or a control method of a mobile terminal according to various embodiments disclosed herein. Also, the operation, the control or the control method of the mobile terminal may be implemented on the mobile terminal by an activation of at least one application program stored in the memory 170.

Hereinafter, description will be given in more detail of the aforementioned components with reference to FIG. 1A, prior to describing various embodiments implemented through the mobile terminal 100.

First, regarding the wireless communication unit 110, the broadcast receiving module 111 is typically configured to receive a broadcast signal and/or broadcast associated information from an external broadcast managing entity via a broadcast channel. The broadcast channel may include a satellite channel, a terrestrial channel, or both. In some embodiments, two or more broadcast receiving modules 111 may be utilized to facilitate simultaneously receiving of two or more broadcast channels, or to support switching among broadcast channels.

The mobile communication module 112 can transmit and/or receive wireless signals to and from one or more network entities. Typical examples of a network entity include a base station, an external mobile terminal, a server, and the like. Such network entities form part of a mobile communication network, which is constructed according to technical standards or communication methods for mobile communications (for example, Global System for Mobile Communication (GSM), Code Division Multi Access (CDMA), CDMA2000 (Code Division Multi Access 2000), EV-DO (Enhanced Voice-Data Optimized or Enhanced Voice-Data Only), Wideband CDMA (WCDMA), High Speed Downlink Packet access (HSDPA), HSUPA (High Speed Uplink Packet Access), Long Term Evolution (LTE), LTE-A (Long Term Evolution-Advanced), and the like).

Examples of wireless signals transmitted and/or received via the mobile communication module 112 include audio call signals, video (telephony) call signals, or various formats of data to support communication of text and multimedia messages.

The wireless Internet module 113 is configured to facilitate wireless Internet access. This module may be internally or externally coupled to the mobile terminal 100. The wireless Internet module 113 may transmit and/or receive wireless signals via communication networks according to wireless Internet technologies.

Examples of such wireless Internet access include Wireless LAN (WLAN), Wireless Fidelity (Wi-Fi), Wi-Fi Direct, Digital Living Network Alliance (DLNA), Wireless Broadband (WiBro), Worldwide Interoperability for Microwave Access (WiMAX), High Speed Downlink Packet Access (HSDPA), HSUPA (High Speed Uplink Packet Access), Long Term Evolution (LTE), LTE-A (Long Term Evolution-Advanced), and the like. The wireless Internet module 113 may transmit/receive data according to one or more of such wireless Internet technologies, and other Internet technologies as well.

In some embodiments, when the wireless Internet access is implemented according to, for example, WiBro, HSDPA, HSUPA, GSM, CDMA, WCDMA, LTE, LTE-A and the like, as part of a mobile communication network, the wireless Internet module 113 performs such wireless Internet access. As such, the Internet module 113 may cooperate with, or function as, the mobile communication module 112.

The short-range communication module 114 is configured to facilitate short-range communications. Suitable technologies for implementing such short-range communications include BLUETOOTH™, Radio Frequency IDentification (RFID), Infrared Data Association (IrDA), Ultra-WideBand (UWB), ZigBee, Near Field Communication (NFC), Wireless-Fidelity (Wi-Fi), Wi-Fi Direct, Wireless USB (Wireless Universal Serial Bus), and the like. The short-range communication module 114 in general supports wireless communications between the mobile terminal 100 and a wireless communication system, communications between the mobile terminal 100 and another mobile terminal 100, or communications between the mobile terminal and a network where another mobile terminal 100 (or an external server) is located, via wireless area networks. One example of the wireless area networks is a wireless personal area networks.

Here, another mobile terminal (which may be configured similarly to mobile terminal 100) may be a wearable device, for example, a smart watch, a smart glass or a head mounted display (HMD), which is able to exchange data with the mobile terminal 100 (or otherwise cooperate with the mobile terminal 100). The short-range communication module 114 may sense or recognize the wearable device, and permit communication between the wearable device and the mobile terminal 100. In addition, when the sensed wearable device is a device which is authenticated to communicate with the mobile terminal 100, the controller 180, for example, may cause transmission of at least part of data processed in the mobile terminal 100 to the wearable device via the short-range communication module 114. Hence, a user of the wearable device may use the data processed in the mobile terminal 100 on the wearable device. For example, when a call is received in the mobile terminal 100, the user may answer the call using the wearable device. Also, when a message is received in the mobile terminal 100, the user can check the received message using the wearable device.

The location information module 115 is generally configured to detect, calculate, derive or otherwise identify a position (or current position) of the mobile terminal. As an example, the location information module 115 includes a Global Position System (GPS) module, a Wi-Fi module, or both. For example, when the mobile terminal uses a GPS module, a position of the mobile terminal may be acquired using a signal sent from a GPS satellite. As another example, when the mobile terminal uses the Wi-Fi module, a position of the mobile terminal can be acquired based on information related to a wireless access point (AP) which transmits or receives a wireless signal to or from the Wi-Fi module. If desired, the location information module 115 may alternatively or additionally function with any of the other modules of the wireless communication unit 110 to obtain data related to the position of the mobile terminal. The location information module 115 is a module used for acquiring the position (or the current position) and may not be limited to a module for directly calculating or acquiring the position of the mobile terminal.

The input unit 120 may be configured to permit various types of inputs (information or signals) to the mobile terminal 100. Examples of such inputs include audio, image, video, data, and user input. Image and video input is often obtained using one or more cameras 121. Such cameras 121 may process image frames of still pictures or video obtained by image sensors in a video or image capture mode. The processed image frames can be displayed on the display unit 151 or stored in memory 170. Meanwhile, the cameras 121 may be arranged in a matrix configuration to permit a plurality of images having various angles or focal points to be input to the mobile terminal 100. Also, the cameras 121 may be located in a stereoscopic arrangement to acquire left and right images for implementing a stereoscopic image.

The microphone 122 processes an external audio signal into electric audio (sound) data. The processed audio data can be processed in various manners according to a function (or an application program) being executed in the mobile terminal 100. If desired, the microphone 122 may include assorted noise removing algorithms to remove unwanted noise generated in the course of receiving the external audio signal.

The user input unit 123 is a component that permits input by a user. Such user input may enable the controller 180 to control operation of the mobile terminal 100. The user input unit 123 may include one or more of a mechanical input element (for example, a mechanical key, a button located on a front and/or rear surface or a side surface of the mobile terminal 100, a dome switch, a jog wheel, a jog switch, and the like), or a touch-sensitive input element, among others. As one example, the touch-sensitive input element may be a virtual key, a soft key or a visual key, which is displayed on a touch screen through software processing, or a touch key which is located on the mobile terminal at a location that is other than the touch screen. On the other hand, the virtual key or the visual key may be displayed on the touch screen in various shapes, for example, graphic, text, icon, video, or a combination thereof.

The sensing unit 140 is generally configured to sense one or more of internal information of the mobile terminal, surrounding environment information of the mobile terminal, user information, or the like, and generate a corresponding sensing signal. The controller 180 generally cooperates with the sending unit 140 to control operation of the mobile terminal 100 or execute data processing, a function or an operation associated with an application program installed in the mobile terminal based on the sensing signal. The sensing unit 140 may be implemented using any of a variety of sensors, some of which will now be described in more detail.

The proximity sensor 141 refers to a sensor to sense presence or absence of an object approaching a surface, or an object located near a surface, by using an electromagnetic field, infrared rays, or the like without a mechanical contact. The proximity sensor 141 may be arranged at an inner region of the mobile terminal covered by the touch screen, or near the touch screen.

The proximity sensor 141, for example, may include any of a transmissive type photoelectric sensor, a direct reflective type photoelectric sensor, a mirror reflective type photoelectric sensor, a high-frequency oscillation proximity sensor, a capacitance type proximity sensor, a magnetic type proximity sensor, an infrared rays proximity sensor, and the like. When the touch screen is implemented as a capacitance type, the proximity sensor 141 can sense proximity of a pointer relative to the touch screen by changes of an electromagnetic field, which is responsive to an approach of an object with conductivity. In this case, the touch screen (touch sensor) may also be categorized as a proximity sensor.

The term "proximity touch" will often be referred to herein to denote the scenario in which a pointer is positioned to be proximate to the touch screen without contacting the touch screen. The term "contact touch" will often be referred to herein to denote the scenario in which a pointer makes physical contact with the touch screen. For the position corresponding to the proximity touch of the pointer relative to the touch screen, such position will correspond to a position where the pointer is perpendicular to the touch screen. The proximity sensor 141 may sense proximity touch, and proximity touch patterns (for example, distance, direction, speed, time, position, moving status, and the like). In general, controller 180 processes data corresponding to proximity touches and proximity touch patterns sensed by the proximity sensor 141, and cause output of visual information on the touch screen. In addition, the controller 180 can control the mobile terminal 100 to execute different operations or process different data (or information) according to whether a touch with respect to a point on the touch screen is either a proximity touch or a contact touch.

A touch sensor can sense a touch (or a touch input) applied to the touch screen, such as display unit 151, using any of a variety of touch methods. Examples of such touch methods include a resistive type, a capacitive type, an infrared type, and a magnetic field type, among others.

As one example, the touch sensor may be configured to convert changes of pressure applied to a specific part of the display unit 151, or convert capacitance occurring at a specific part of the display unit 151, into electric input signals. The touch sensor may also be configured to sense not only a touched position and a touched region, but also touch pressure and/or touch capacitance. A touch object is generally used to apply a touch input to the touch sensor. Examples of typical touch objects include a finger, a touch pen, a stylus pen, a pointer, or the like.

When a touch input is sensed by a touch sensor, corresponding signals may be transmitted to a touch controller. The touch controller may process the received signals, and then transmit corresponding data to the controller 180. Accordingly, the controller 180 may sense which region of the display unit 151 has been touched. Here, the touch controller may be a component separate from the controller 180, the controller 180, and combinations thereof.

Meanwhile, the controller 180 may execute the same or different controls according to a type of touch object that touches the touch screen or a touch key provided in addition to the touch screen. Whether to execute the same or different control according to the object which provides a touch input may be decided based on a current operating state of the mobile terminal 100 or a currently executed application program, for example.

The touch sensor and the proximity sensor may be implemented individually, or in combination, to sense various types of touches. Such touches includes a short (or tap) touch, a long touch, a multi-touch, a drag touch, a flick touch, a pinch-in touch, a pinch-out touch, a swipe touch, a hovering touch, and the like.

If desired, an ultrasonic sensor may be implemented to recognize position information relating to a touch object using ultrasonic waves. The controller 180, for example, may calculate a position of a wave generation source based on information sensed by an illumination sensor and a plurality of ultrasonic sensors. Since light is much faster than ultrasonic waves, the time for which the light reaches the optical sensor is much shorter than the time for which the ultrasonic wave reaches the ultrasonic sensor. The position of the wave generation source may be calculated using this fact. For instance, the position of the wave generation source may be calculated using the time difference from the time that the ultrasonic wave reaches the sensor based on the light as a reference signal.

The camera 121, which has been depicted as a component of the input unit 120, typically includes at least one a camera sensor (CCD, CMOS etc.), a photo sensor (or image sensors), and a laser sensor.

Implementing the camera 121 with a laser sensor may allow detection of a touch of a physical object with respect to a 3D stereoscopic image. The photo sensor may be laminated on, or overlapped with, the display device. The photo sensor may be configured to scan movement of the physical object in proximity to the touch screen. In more detail, the photo sensor may include photo diodes and transistors at rows and columns to scan content received at the photo sensor using an electrical signal which changes according to the quantity of applied light. Namely, the photo sensor may calculate the coordinates of the physical object according to variation of light to thus obtain position information of the physical object.

The display unit 151 is generally configured to output information processed in the mobile terminal 100. For example, the display unit 151 may display execution screen information of an application program executing at the mobile terminal 100 or user interface (UI) and graphic user interface (GUI) information in response to the execution screen information.

Also, the display unit 151 may be implemented as a stereoscopic display unit for displaying stereoscopic images.

A typical stereoscopic display unit may employ a stereoscopic display scheme such as a stereoscopic scheme (a glass scheme), an auto-stereoscopic scheme (glassless scheme), a projection scheme (holographic scheme), or the like.

The audio output module 152 is generally configured to output audio data. Such audio data may be obtained from any of a number of different sources, such that the audio data may be received from the wireless communication unit 110 or may have been stored in the memory 170. The audio data may be output during modes such as a signal reception mode, a call mode, a record mode, a voice recognition mode, a broadcast reception mode, and the like. The audio output module 152 can provide audible output related to a particular function (e.g., a call signal reception sound, a message reception sound, etc.) performed by the mobile terminal 100. The audio output module 152 may also be implemented as a receiver, a speaker, a buzzer, or the like.

A haptic module 153 can be configured to generate various tactile effects that a user feels, perceive, or otherwise experience. A typical example of a tactile effect generated by the haptic module 153 is vibration. The strength, pattern and the like of the vibration generated by the haptic module 153 can be controlled by user selection or setting by the controller. For example, the haptic module 153 may output different vibrations in a combining manner or a sequential manner.

Besides vibration, the haptic module 153 can generate various other tactile effects, including an effect by stimulation such as a pin arrangement vertically moving to contact skin, a spray force or suction force of air through a jet orifice or a suction opening, a touch to the skin, a contact of an electrode, electrostatic force, an effect by reproducing the sense of cold and warmth using an element that can absorb or generate heat, and the like.

The haptic module 153 can also be implemented to allow the user to feel a tactile effect through a muscle sensation such as the user's fingers or arm, as well as transferring the tactile effect through direct contact. Two or more haptic modules 153 may be provided according to the particular configuration of the mobile terminal 100.

An optical output module 154 can output a signal for indicating an event generation using light of a light source. Examples of events generated in the mobile terminal 100 may include message reception, call signal reception, a missed call, an alarm, a schedule alarm, an email reception, information reception through an application, and the like.

A signal output by the optical output module 154 may be implemented in such a manner that the mobile terminal emits monochromatic light or light with a plurality of colors. The signal output may be terminated as the mobile terminal senses that a user has checked the generated event, for example.

The interface unit 160 serves as an interface for external devices to be connected with the mobile terminal 100. For example, the interface unit 160 can receive data transmitted from an external device, receive power to transfer to elements and components within the mobile terminal 100, or transmit internal data of the mobile terminal 100 to such external device. The interface unit 160 may include wired or wireless headset ports, external power supply ports, wired or wireless data ports, memory card ports, ports for connecting a device having an identification module, audio input/output (I/O) ports, video I/O ports, earphone ports, or the like.

The identification module may be a chip that stores various information for authenticating authority of using the mobile terminal 100 and may include a user identity module (UIM), a subscriber identity module (SIM), a universal subscriber identity module (USIM), and the like. In addition, the device having the identification module (also referred to herein as an "identifying device") may take the form of a smart card. Accordingly, the identifying device can be connected with the terminal 100 via the interface unit 160.

When the mobile terminal 100 is connected with an external cradle, the interface unit 160 can serve as a passage to allow power from the cradle to be supplied to the mobile terminal 100 or may serve as a passage to allow various command signals input by the user from the cradle to be transferred to the mobile terminal there through. Various command signals or power input from the cradle may operate as signals for recognizing that the mobile terminal is properly mounted on the cradle.

The memory 170 can store programs to support operations of the controller 180 and store input/output data (for example, phonebook, messages, still images, videos, etc.). The memory 170 may store data related to various patterns of vibrations and audio which are output in response to touch inputs on the touch screen.

The memory 170 may include one or more types of storage mediums including a flash memory type, a hard disk type, a solid state disk (SSD) type, a silicon disk drive (SDD) type, a multimedia card micro type, a card-type memory (e.g., SD or DX memory, etc), a Random Access Memory (RAM), a Static Random Access Memory (SRAM), a Read-Only Memory (ROM), an Electrically Erasable Programmable Read-Only Memory (EEPROM), a Programmable Read-Only memory (PROM), a magnetic memory, a magnetic disk, an optical disk, and the like. The mobile terminal 100 may also be operated in relation to a network storage device that performs the storage function of the memory 170 over a network, such as the Internet.

The controller 180 may typically control the general operations of the mobile terminal 100. For example, the controller 180 may set or release a lock state for restricting a user from inputting a control command with respect to applications when a status of the mobile terminal meets a preset condition.

The controller 180 can also perform the controlling and processing associated with voice calls, data communications, video calls, and the like, or perform pattern recognition processing to recognize a handwriting input or a picture drawing input performed on the touch screen as characters or images, respectively. In addition, the controller 180 can control one or a combination of those components in order to implement various exemplary embodiments disclosed herein.

The power supply unit 190 receives external power or provide internal power and supply the appropriate power required for operating respective elements and components included in the mobile terminal 100. The power supply unit 190 may include a battery, which is typically rechargeable or be detachably coupled to the terminal body for charging.

The power supply unit 190 may include a connection port. The connection port may be configured as one example of the interface unit 160 to which an external charger for supplying power to recharge the battery is electrically connected.

As another example, the power supply unit 190 may be configured to recharge the battery in a wireless manner without use of the connection port. In this example, the power supply unit 190 can receive power, transferred from an external wireless power transmitter, using at least one of an inductive coupling method which is based on magnetic induction or a magnetic resonance coupling method which is based on electromagnetic resonance.

Various embodiments described herein may be implemented in a computer-readable medium, a machine-readable medium, or similar medium using, for example, software, hardware, or any combination thereof.

Figure 1B:
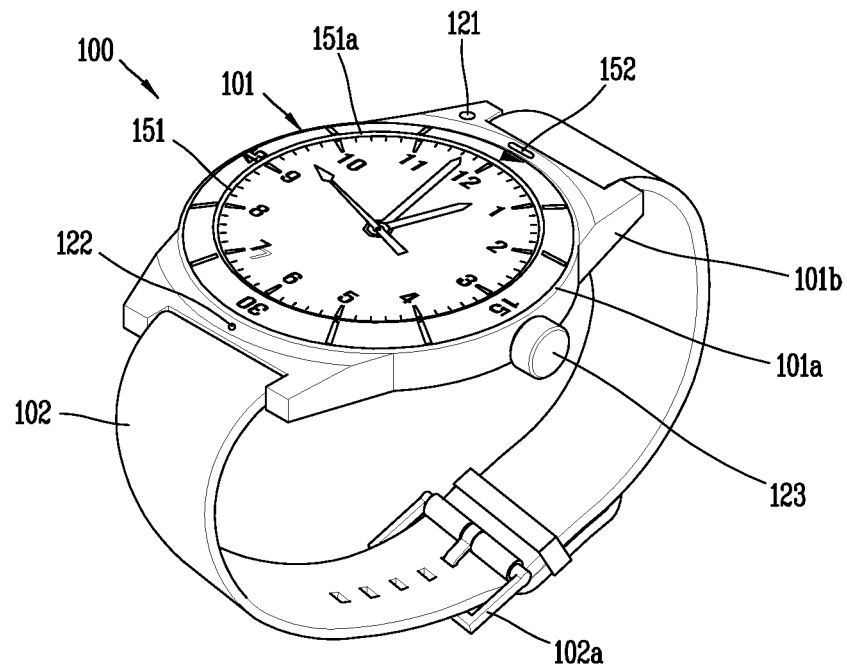
FIG. 1B is a view of a watch type terminal according to one exemplary embodiment, viewed in one direction.

FIG. 1B is a view of a watch type mobile terminal in accordance with one exemplary embodiment, viewed in one direction.

Referring to FIG. 1B, the watch-type mobile terminal 100 includes a main body 101 with a display unit 151 and a band 102 connected to the main body 101 to be wearable on a wrist.

The main body 101 may include a case having a certain appearance. As illustrated, the case may include a first case 101a and a second case 101b cooperatively defining an inner space for accommodating various electronic components. Other configurations are possible. For instance, a single case may alternatively be implemented, with such a case being configured to define the inner space, thereby implementing a mobile terminal 100 with a uni-body.

The watch-type mobile terminal 100 can perform wireless communication, and an antenna for the wireless communication can be installed in the main body 101. The antenna may extend its function using the case. For example, a case including a conductive material may be electrically connected to the antenna to extend a ground area or a radiation area.

The display unit 151 is shown located at the front side of the main body 101 so that displayed information is viewable to a user. The display unit 151 includes a touch sensor so that the display unit can function as a touch screen. As illustrated, a window 151a is positioned on the first case 101a to form a front surface of the main body together with the first case 101a.

The illustrated embodiment includes audio output module 152, a camera 121, a microphone 122, and a user input unit 123. When the display unit 151 is implemented as a touch screen, it may function as the user input unit 123, and a separate key may thus not be provided on the main body 101.

The band 102 is commonly worn on the user's wrist and may be made of a flexible material for facilitating wearing of the device. As one example, the band 102 may be made of fur, rubber, silicon, synthetic resin, or the like. The band 102 may also be configured to be detachable from the main body 101. Accordingly, the band 102 may be replaceable with various types of bands according to a user's preference.

Meanwhile, the band 102 may be used for extending the performance of the antenna. For example, the band may include therein a ground extending portion (not shown) electrically connected to the antenna to extend a ground area.

The band 102 may include a fastener 102a. The fastener 102a may be implemented into a buckle type, a snap-fit hook structure, a Velcro® type, or the like, and include a flexible section or material. The drawing illustrates an example that the fastener 102a is implemented using a buckle.

Figure 1C:
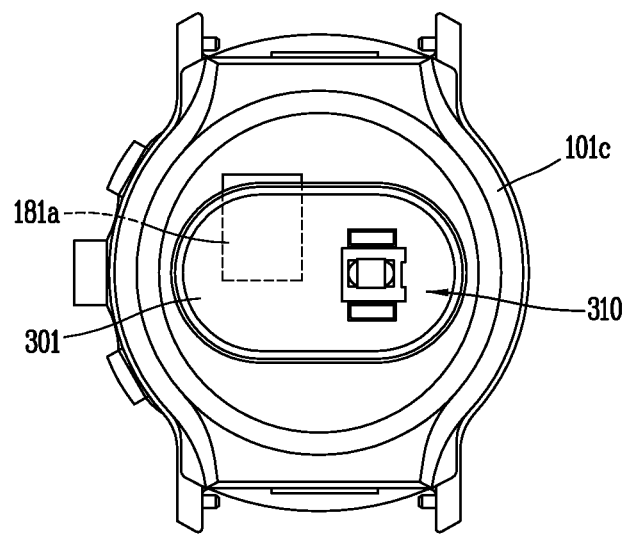
FIG. 1C is a conceptual view of a main body of a watch type terminal according to one exemplary embodiment, viewed in one direction.

FIG. 1C is a conceptual view of a main body of a watch type terminal according to one exemplary embodiment, viewed in one direction.

The watch type terminal 100 according to the present invention includes a sensor module for measuring a biometric signal. The watch type terminal 100 according to this exemplary embodiment is provided with a rear cover 101c on a surface facing the display unit 151. The rear cover 101c forms an inner space together with the second case 101b.

The rear cover 101c is provided with an accommodating unit 300 in which a first sensing unit 310 is accommodated. The accommodating unit 300 may protrude more than an outer surface of the rear cover 101, and be provided with a window having a transparent area in which light output from the first sensing unit 310 and reflected by the user's body is received. The accommodating unit 300 may accommodate therein a user identity module (UIM), a subscriber identity module (SIM), a universal subscriber identity module (USIM), and the like.

The accommodating unit 300 which protrudes more than the second case 101b may allow the first sensing unit 310 to be closely adhered to one area of the user's body, which may result in minimizing a leakage of light emitted.

Figure 2A:
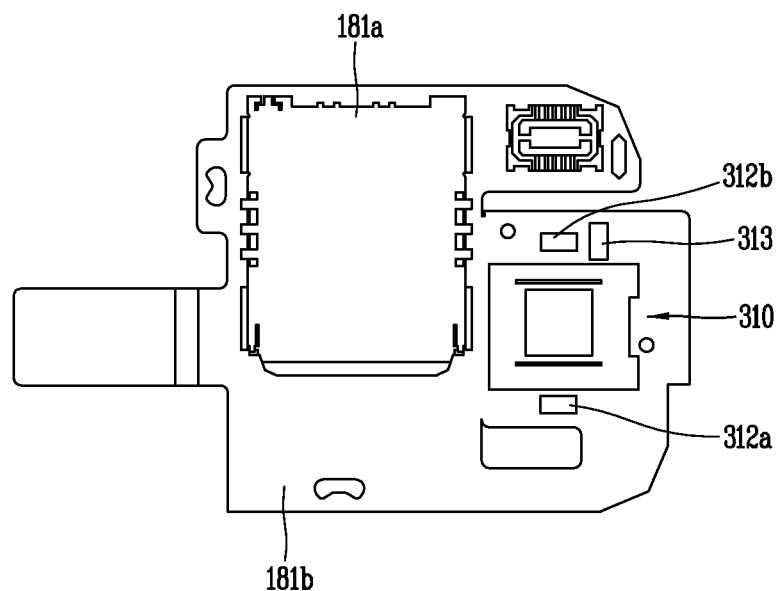
FIGS. 2A and 2B are conceptual views illustrating a configuration and an arrangement structure of a first sensing unit.
Figure 2B:
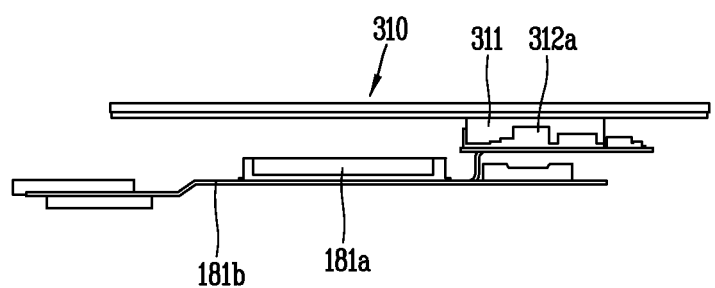

FIGS. 2A and 2B are conceptual views illustrating a configuration and an arrangement structure of a first sensing unit.

As illustrated in FIGS. 2A and 2B, a chip 181a and the first sensing unit 310 are provided on a circuit board 181b. The first sensing unit 310 includes a light receiving sensor 311, a first light emitting device 312a, and a second light emitting device 312b. The first and second lighting devices 312a and 312b are disposed on the circuit board 181b with the light receiving sensor 311 interposed therebetween. The light receiving sensor 311 and the first and second light emitting devices 312a and 312b are independently fixed to the circuit board 181b, and spaced apart from one another with preset distances. Also, an IR sensor 313 is disposed adjacent to the second light emitting device 312b. The light emitting devices may be implemented as light-emitting diodes (LEDs) outputting green light.

The first and second light emitting devices 312a and 312b output green light. The green light output from the first and second light emitting devices 312a and 312b is reflected by a user's skin to be received into the light receiving sensor 311.

Transmittance is reduced for light with a short wavelength and increased for light with a long wavelength. In order for the first sensing unit 310 as a PPG sensor to measure a biometric signal (changes in heartbeats), the output light should reach up to a skin depth in which a blood vessel is located to allow for measuring changes in blood flow. However, if the output light goes into the user's body by more than the skin depth where the blood vessel is located, the light may be absorbed into a tissue or bone. In general, a wrist of a body has a depth up to a blood vessel deeper than a finger. Therefore, the transmittance of the green light is proper to reach up to the blood vessel of the wrist.

The sensing unit according to this embodiment applies different strength and color of output light according to a color of a skin or a skin with a great depth up to a blood vessel. This feature will be described in detail later with reference to FIG. 9 and the following drawings.

Figure 3A:
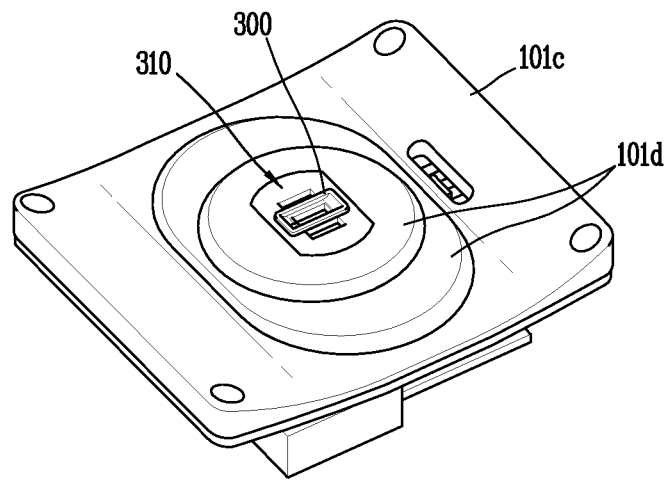
FIGS. 3A and 3B are conceptual views illustrating a structure of an accommodating unit for accommodating the first sensing unit therein.
Figure 3B:
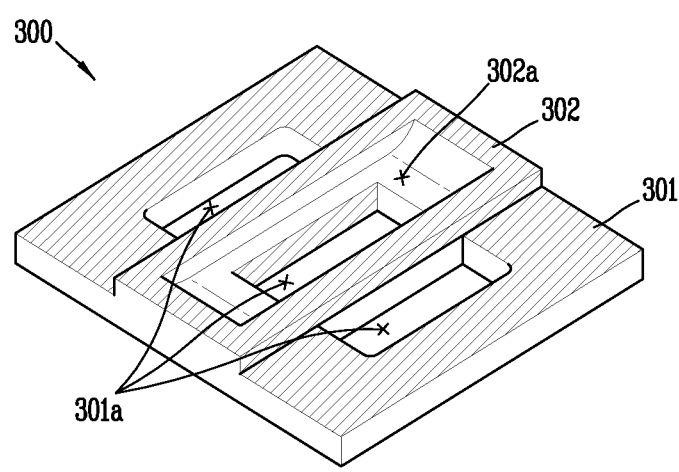

FIGS. 3A and 3B are conceptual views illustrating a structure of an accommodating unit for accommodating a first sensing unit.

FIG. 3A is a conceptual view illustrating a structure of the accommodating unit 300 for accommodating the first sensing unit 310. One surface of the rear cover 101c on which the first sensing unit 310 is disposed is formed as a concavely-curved surface. A supporting portion 101d may be formed on the concavely-curved surface. The supporting portion 101d may be disposed on a center of the concavely-curved surface so as to be closely adhered to the user's body.

The accommodating unit 300 is disposed on one area of the supporting portion 101d. For example, the accommodating unit 300 is formed on a center of the supporting portion 101d. Referring to FIG. 3B, the accommodating unit 300 includes a base portion 301, and a mask portion 302 protruding from the base portion 301. The base portion 301 includes three receiving grooves 301a. The first and second light emitting devices 312a and 312b and the light receiving sensor 311 are mounted in the receiving grooves 301a, respectively.

Meanwhile, the mask portion 302 includes a recess 302a communicating with one of the receiving grooves 301a. The mask portion 302 may be formed in a shape of a closed loop. Or, the mask portion 302 may be disposed between each of the first and second light emitting devices 312a and 312b and the light receiving sensor 311. The mask portion 302 is brought into contact with the user's body when the user wears the watch type terminal 100, and blocks an introduction of light into the light receiving sensor 311. Also, the mask portion 302 may prevent the light emitted from the first and second light emitting devices 312a and 312b from being introduced directly into the light receiving sensor 311 without reaching the user's body. The base portion 301 and the mask portion 302 may be integrally formed with each other.

Figure 3C:
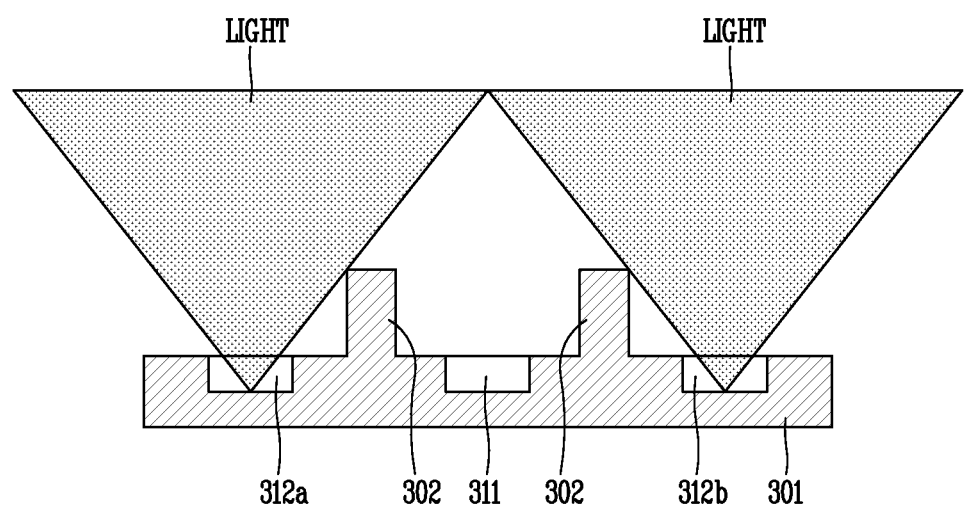
FIG. 3C is a conceptual view of the first sensing unit accommodated in the accommodating unit.

FIG. 3C is a conceptual view of the first sensing unit accommodated in the accommodating unit.

As illustrated in FIG. 3C, the light receiving sensor 311, and the first and second light emitting devices 312a and 312b are disposed in the receiving grooves 301a formed on the base portion 301. The mask portion 302 is disposed between the first light emitting device 312a and the light receiving sensor 311 and between the second light emitting device 312b and the light receiving sensor 311.

Light output from each of the first and second light emitting devices 312a and 312b is not introduced into the light receiving sensor 311 by the mask portion 302.

The sensing unit according to the present invention can minimize light introduced into the light receiving sensor even when the light emitting devices and the light receiving sensor are individually disposed on the circuit board.

Figure 4A:
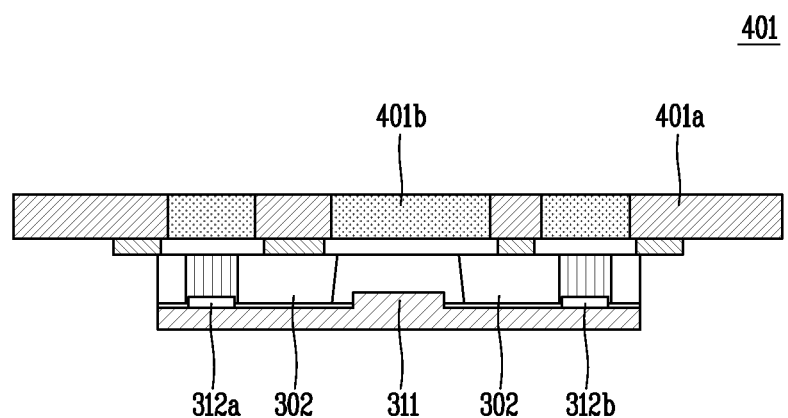
FIGS. 4A and 4B are conceptual views illustrating a structure of a window according to one exemplary embodiment.
Figure 4B:
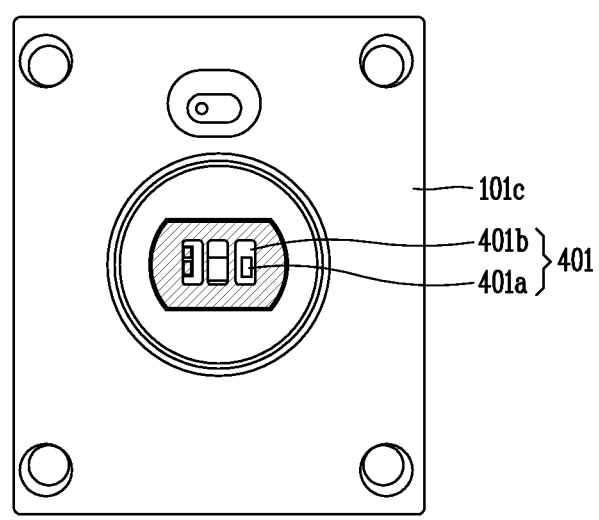

FIGS. 4A and 4B are conceptual views illustrating a structure of a window according to one exemplary embodiment.

As illustrated in FIG. 4A, a first window 401 includes a mask area 401a and transparent areas 401b. The mask area 401a corresponds to a printed area through which light cannot be transmitted. The mask area 401a and the transparent areas 401b preferably have substantially the same thickness. The first and second light emitting devices 312a and 312b and the light receiving sensor 311 are arranged in the accommodating unit 300, and the first window 401 is disposed on the accommodating unit 300. The first window 401 is coupled to the rear cover 101c so as to define appearance of the watch type terminal 100.

The transparent areas 401b of the first window 401 correspond to the first and second light emitting devices 312a and 312b and the light receiving sensor 311, respectively. The mask area 401a of the first window 401 is disposed between the first and second light emitting devices 312a and 312b and the light receiving sensor 311. The mask area 401a may be brought into contact with the mask portion 302 of the accommodating unit 300. Accordingly, light output from each of the first and second light emitting devices 312a and 312b cannot be introduced into the light receiving sensor 311 and thus can reach the contacted body. Also, the light receiving sensor 311 is surrounded by the mask area 401a, and thus a problem that the other light except for the light output from the light emitting devices is introduced into the light receiving sensor 311 can be prevented.

As illustrated in FIG. 4B, the first and second light emitting devices 312a and 312b and the light receiving sensor 311 are visually exposed through the transparent area 401b of the first window 401 coupled to the rear cover 101c. Accordingly, the leakage of light which is likely to be caused when the light emitting devices and the light receiving sensor are individually disposed can be prevented.

FIGS. 5A to 5E are conceptual views illustrating an assembling structure of a sensing unit in accordance with another exemplary embodiment.

The main body of the watch type terminal 100 includes a protruding portion 101e protruding from one area of the rear cover 101c. The protruding portion 101e is preferably formed on a center of the rear cover 101c. A protruding area A formed by the protruding portion 101e is closely adhered to a wrist when the watch type terminal 100 is worn on the wrist.

The accommodating unit 300 and the window 401 are mounted on the protruding portion 101e. The window 401 may form the same surface as an outer surface of the protruding portion 101e. Accordingly, when the watch type terminal 100 is worn on the user's wrist, the first and second light emitting devices 312a and 312b and the light receiving sensor 311 received in the accommodating unit 300 may be closely adhered to the wrist.

Figure 5A:
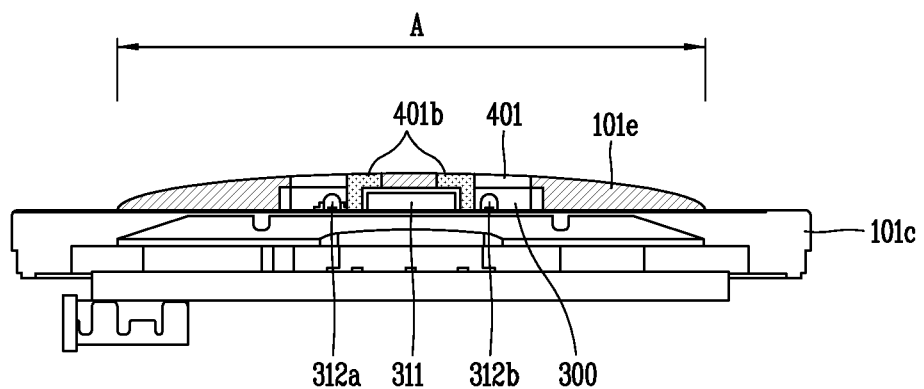
FIGS. 5A to 5E are conceptual views illustrating an assembling structure of a sensing unit in accordance with another exemplary embodiment.
Figure 5B:
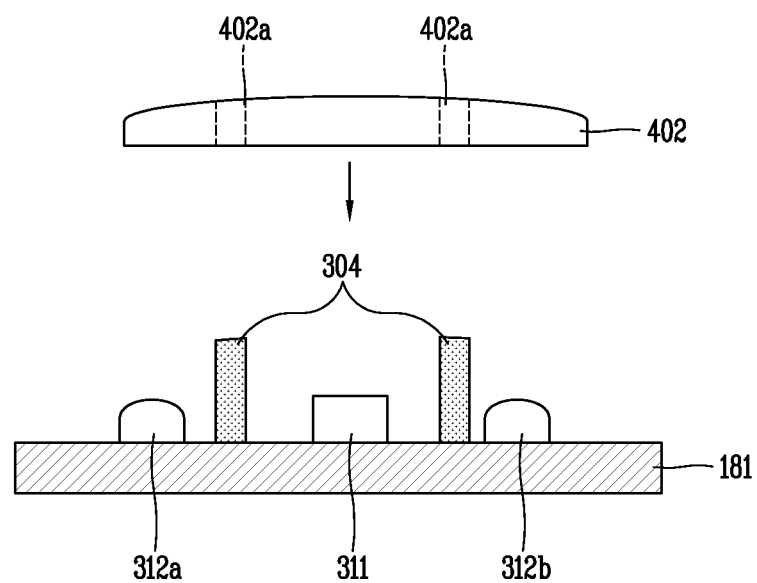

Hereinafter, a structure in which first light shielding barrier walls 304 and a second window 402 are coupled to each other will be described with reference to FIG. 5B. The first and second light emitting devices 312a and 312b and the light receiving sensor 311 are mounted on a circuit board 181. The first and second light emitting devices 312a and 312b and the light receiving sensor 311 are spaced apart from one another with preset distances. First light shielding barrier walls 304 are disposed between the first and second light emitting devices 312a and 312b and the light receiving sensor 311. The first light shielding barrier walls 304 are preferably higher than the first and second light emitting devices 312a and 312b and the light receiving sensor 311 in view of height.

The second window 402 according to this embodiment includes insertion holes 402a. The insertion hole 402a are formed in a thickness direction, and end portions of the first light shielding barrier walls 304 are inserted into the insertion holes 402a. The end portions of the first light shielding barrier walls 304 may be externally exposed through the insertion holes 402a.

The first light shielding barrier walls 304 may be made of rubber, and also made of an opaque material to prevent transmission of light. The first light shielding barrier walls 304 can prevent a problem that light output from the light emitting devices is incident on the light receiving sensor without reaching the user's body. The first light shielding barrier walls 304 are preferably formed to surround at least one area of the light receiving sensor 311, and disposed between the light emitting devices and the light receiving sensor according to a number of the light emitting devices.

According to this embodiment disclosed herein, a light shielding area does not have to be printed on the window by virtue of the light shielding barrier walls which are formed along with the light receiving sensor and the light emitting devices, and a wrong movement of light can be prevented. Also, since the light shielding barrier walls are coupled to the window, a light leakage can be prevented by the fixed light shielding barrier walls even when the window is moved due to an assembly error or the like.

Figure 5C:
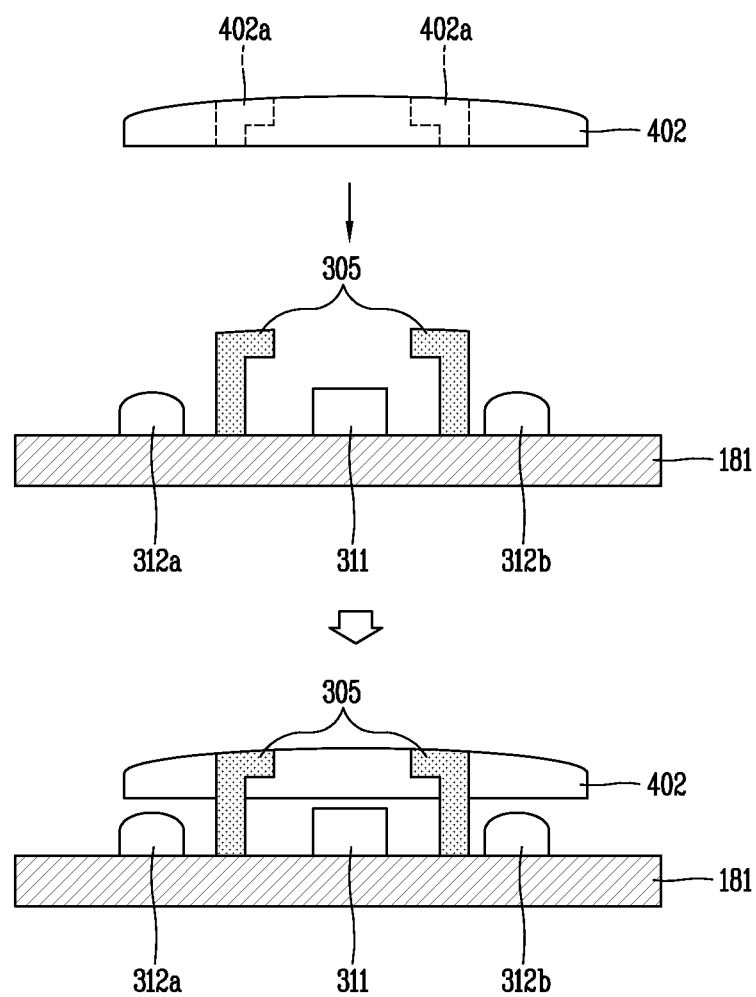

FIG. 5C is a conceptual view illustrating a structure of light shielding barrier walls in accordance with another exemplary embodiment. Second light shielding barrier walls 305 are inserted into insertion holes 402a formed through the second window 402. Each of the second light shielding barrier walls 305 is bent at an end portion thereof. The pair of second light shielding barrier walls 305 include such bent structures which are bent to face each other. The bent structures are formed higher than the light receiving sensor 311, and spaced apart from each other not to obscure the light receiving sensor 311.

Meanwhile, the insertion holes 402a of the second window 402 may include recess areas, respectively, to fix the bent structures.

The second light shielding barrier walls 305 each having the bent structure can be more stably fixed to the second window 402 by virtue of the bent structures, and effectively block other external light introduced into the light receiving sensor 311.

Figure 5D:
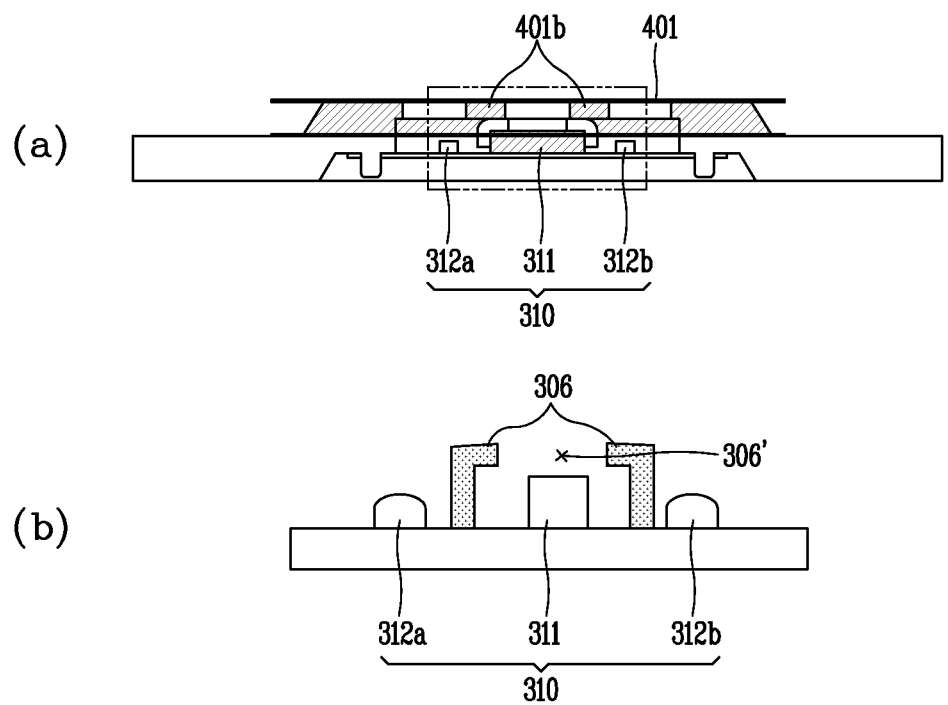
Figure 5E:
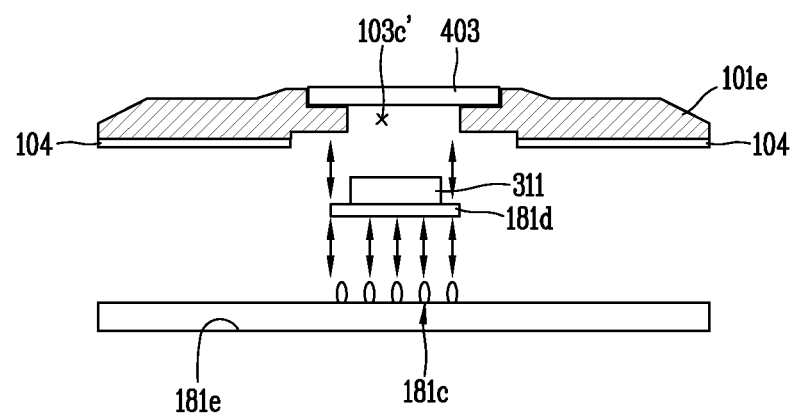

Hereinafter, a structure of a third light shielding barrier wall 306 which forms an inner space fully surrounding side surfaces of the light receiving sensor will be described with reference to FIG. 5D. The third light shielding barrier wall 306 forms an opening 306'.

The third light shielding barrier wall 306 is fixed on the circuit board 181 with the light receiving sensor 311, and the opening 306' is disposed to correspond to the light receiving sensor 311. Accordingly, the other area except for a light-incident area of the light receiving sensor 311 may be shielded from light. The first and second light emitting devices 312a and 312b are disposed outside the third light shielding barrier wall 306 and the window is disposed on the third light shielding barrier wall 306.

According to these embodiments, the light receiving sensor and the light emitting devices may be spaced apart by specific distances with interposing the light shielding barrier walls between the devices, thereby implementing light shielding between the devices without an additional assembly structure. This may result in preventing a crosstalk.

Hereinafter, a structure in which a sensor unit mounted on a circuit board 181d and a window are attached to each other will be described with reference to FIG. 5D. The sensor unit includes at least one light emitting device and at least one light receiving sensor 311 all mounted on the circuit board 181d in an independent manner.

Meanwhile, one area of a protruding portion 101e forms an opening 101e', and a third window 403 is inserted into the opening 101e'. The opening 101e' and the third window 403 have substantially the same shape. The sensor unit mounted on the circuit board 181d is attached to the opening 101e'. The third window 403 and the sensor unit may be adhered to each other by an adhesive tape or the like.

The circuit board 181d and a main circuit board 181e are connected to each other by a connector 181c. A spacing may be formed between the circuit board 181d and the main circuit board 181e, and the connector 181c may be implemented as C-clips and the like.

The sensor unit according to this embodiment may include light shielding barrier walls disposed between neighboring devices, and each device may be fixed by an accommodating unit. According to this embodiment, the light receiving sensor 311 can be fixed to the window, thereby efficiently utilizing an inner space.

Figure 6A:
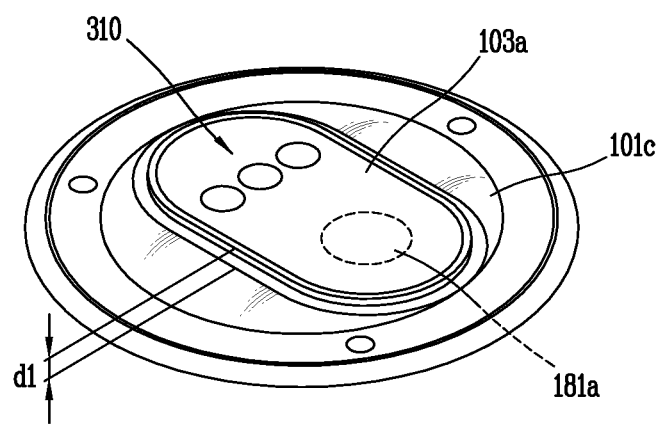
FIGS. 6A to 6C are conceptual views illustrating structures of a protruding portion.
Figure 6A:
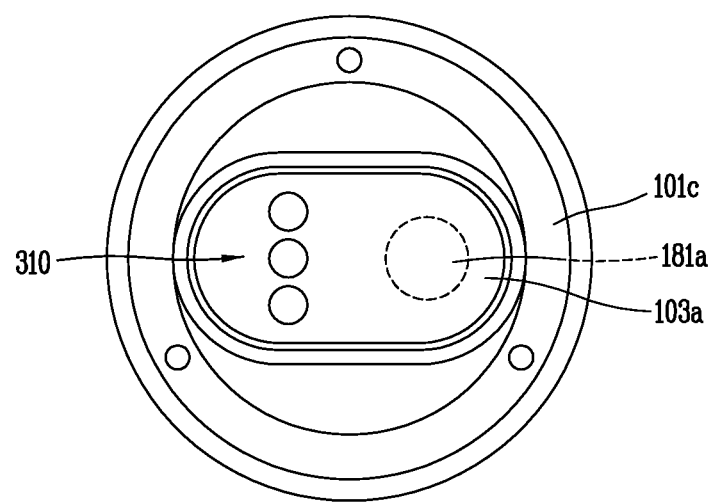
Figure 6B:
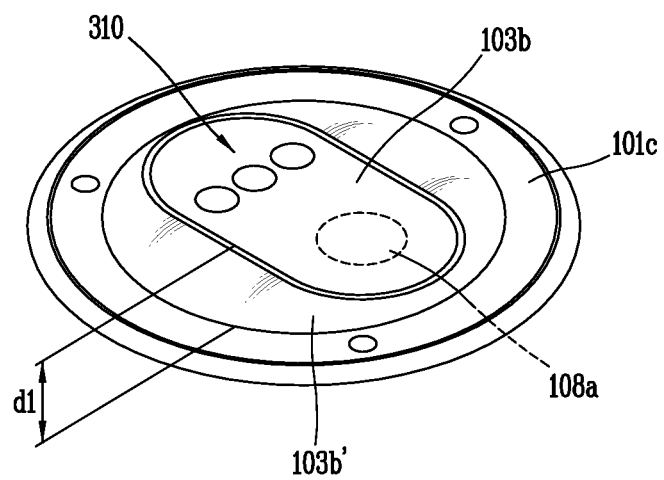
Figure 6B:
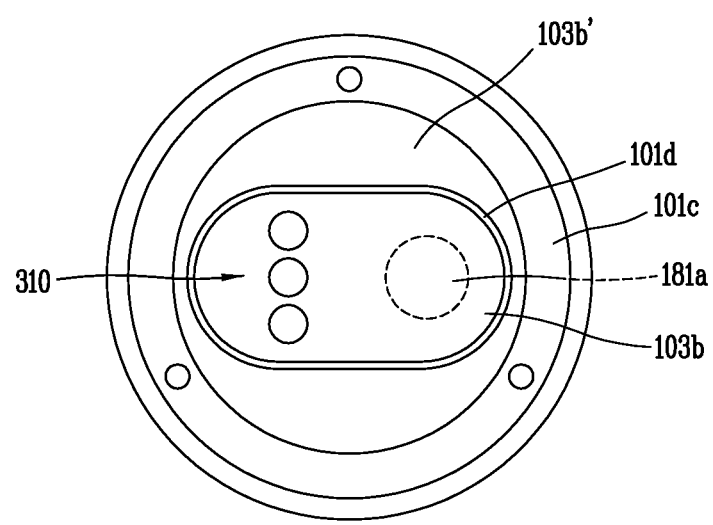
Figure 6C:
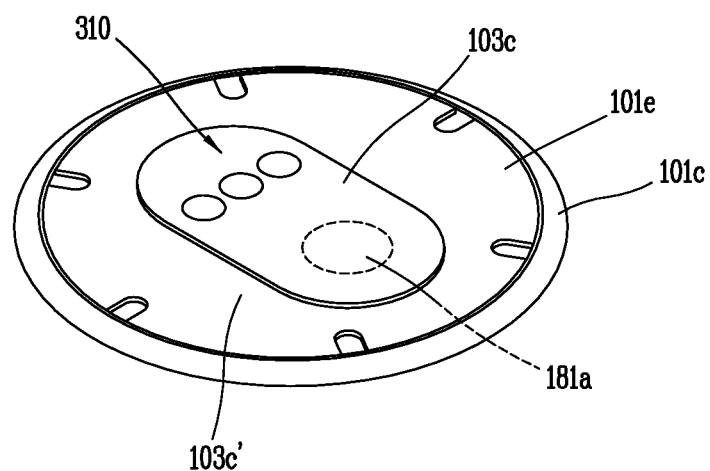
Figure 6C:
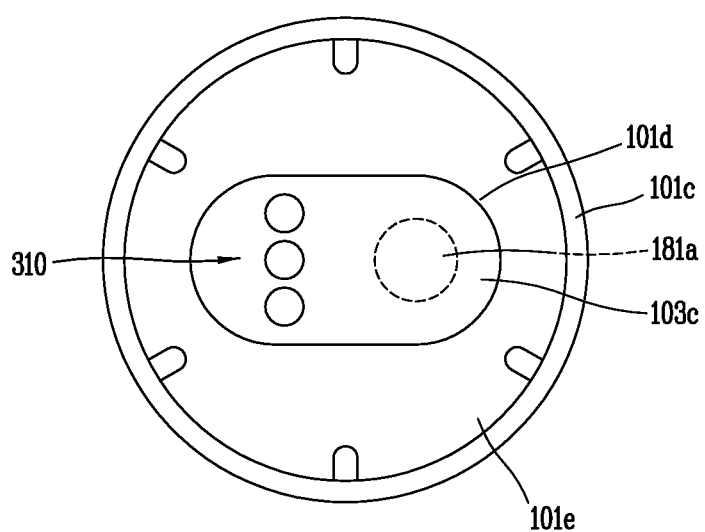

FIGS. 6A to 6C are conceptual views illustrating various structures of a protruding portion.

Referring to FIG. 6A, a first protruding portion 103a is formed on a central area of the rear cover 101c. The first protruding portion 103a protrudes from an outer surface of the rear cover 101c up to a specific height dl to have a section in a specific shape. The first protruding portion 103a forms a flat surface. The sensing unit 310 and the chip 181a may be disposed within the first protruding portion 103a.

Referring to FIG. 6B, a second protruding portion 103b is formed on a central area of the rear cover 101c. The second protruding portion 103b includes an inclined portion 103b' which is getting narrower with forming an inclined plane. The second protruding portion 103b is getting higher toward a center by virtue of the inclined portion 103b'. The highest second protruding portion 103b may have a specific height dl.

Referring to FIG. 6C, a third protruding portion 103c includes an extended inclined portion 103c'. The extended inclined portion 103c' upwardly extends from an area adjacent to an edge area of the rear cover 101c up to the central area of the rear cover 101c in an inclined manner. That is, the third protruding portion 103c may not form a step with the rear cover 101c and improve a sense of unity.

The sensing unit can be closely adhered to the user's body by the protruding portion, such as the first to third protruding portions 103a, 103b and 103c, and the sensing unit and the chip can be received within an ensured inner space.

Figure 7:
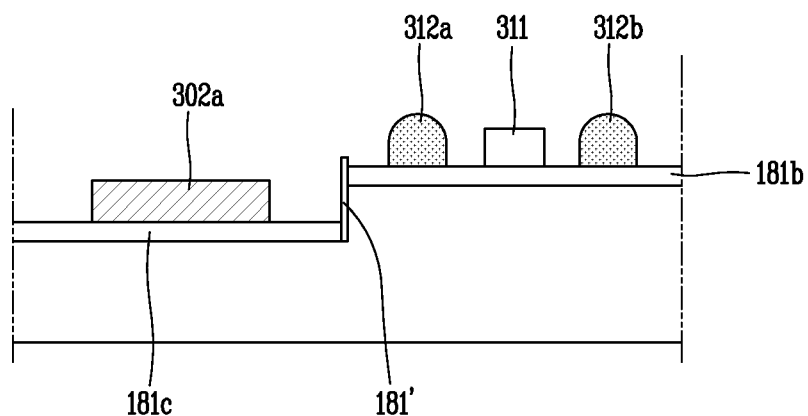
FIG. 7 is a conceptual view illustrating an accommodating structure of a sensing unit and a chip.

FIG. 7 is a conceptual view illustrating an accommodating structure of a sensing unit and a chip.

Referring to FIG. 7, the first circuit board 181b and the second circuit board 181c are connected to each other by a flexible circuit board 181'. The first and second circuit boards 181b and 181c are disposed within inner frames (shield cans) forming a step therebetween. The flexible circuit board 181' is disposed to overlap the step, to electrically connect the first and second circuit boards 181b and 181c to each other.

The first and second light emitting devices 312a and 312b and the light receiving sensor 311 may be mounted on the first circuit board 181b, and the chip 181a may be mounted on the second circuit board 181c.

Figure 8A:
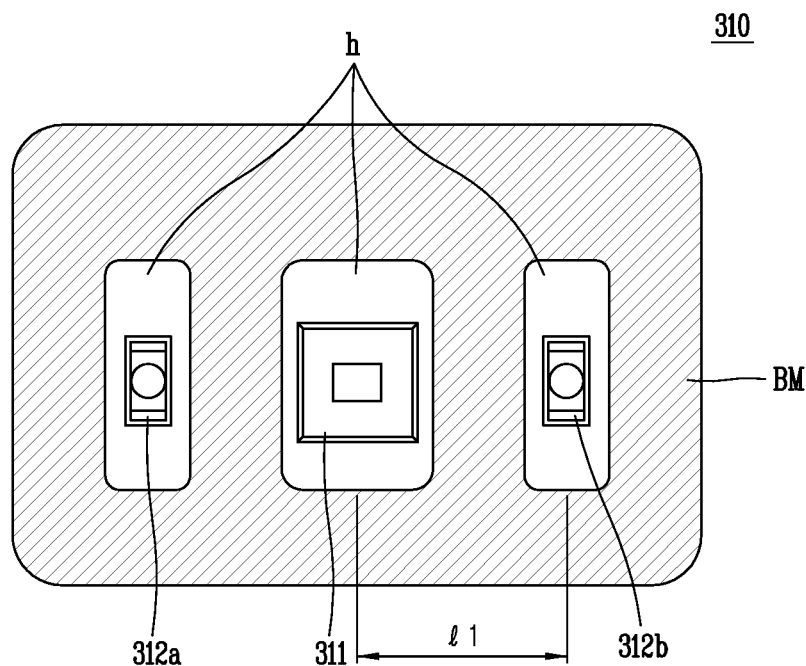
FIGS. 8A to 8C are conceptual views illustrating arrangement structures of a sensing unit including one light receiving sensor and green light emitting devices.
Figure 8B:
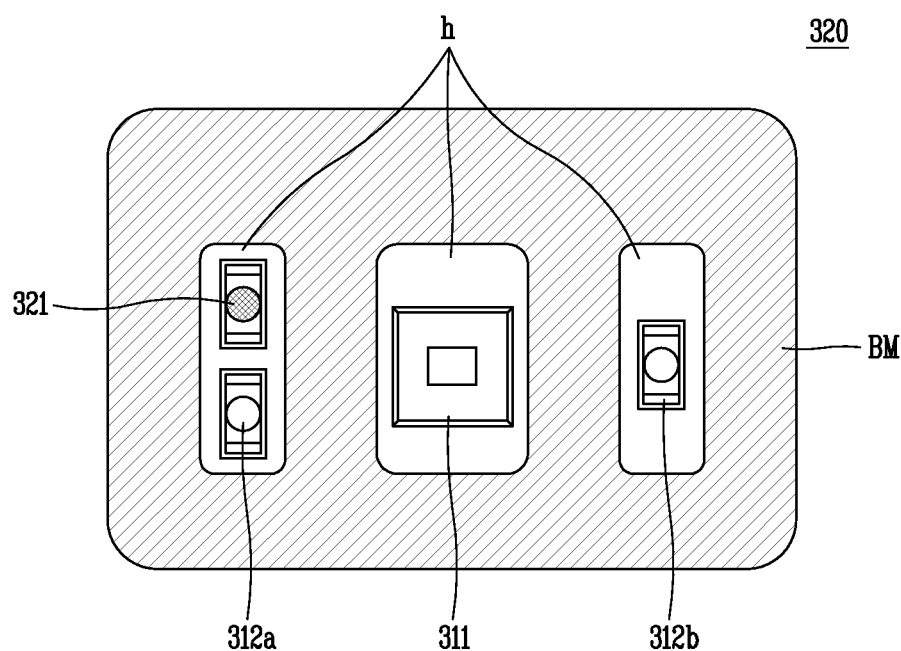
Figure 8C:
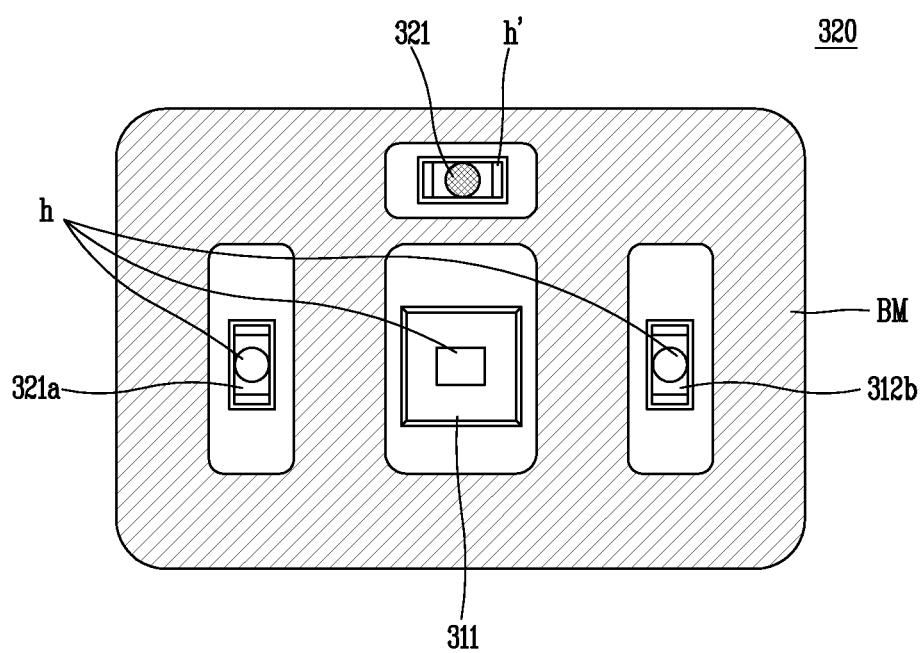

FIGS. 8A to 8C are conceptual views illustrating an arrangement structure of a sensing unit including one light receiving sensor and green light emitting devices.

FIG. 8A illustrates an arrangement structure of the first sensing unit 310 having a light receiving sensor 311 and first and second green light emitting devices 312a and 312b. The first sensing unit 310 which includes the first and second green light emitting devices 312a and 312b is visually exposed through transparent areas h formed by a mask area BM. The transparent areas h are preferably formed to be greater in size than the devices not to obscure the devices.

The first and second green light emitting devices 312a and 312b are disposed to be symmetrical to each other on the basis of the light receiving sensor 311. The first green light emitting device 312a and the light receiving sensor 311 are spaced apart from each other by a preset first length l1.

The second sensing unit 320 according to FIG. 8B includes a light receiving sensor 311, first and second green light emitting devices 312a and 312b, and an IR light emitting device 321. The controller 180 collects biometric signals using green light output from the first and second green light emitting devices 312a and 312b. On the other hand, the controller 180 may determine a worn state of the watch type terminal using IR light output from the IR light emitting device 321.

For example, the controller 180 may detect whether or not the watch type terminal has been worn by activating the IR light emitting device 321 more frequently than the green light emitting devices. That is, the IR light emitting device 321 may output IR light at a preset period even in a state that a specific function is not activated by the watch type terminal 100.

The first and second green light emitting devices 312a and 312b are disposed symmetrical to each other on the basis of the light receiving sensor 311. The IR light emitting device 321 may be disposed adjacent to one of the first and second green light emitting devices 312a and 312b.

For example, the IR light emitting device 321 may be disposed at a position overlapping the transparent area h so as to output light through the transparent area h corresponding to the first green light emitting device 312a.

Meanwhile, referring to FIG. 8C, an additional transparent area h' corresponding to the IR light emitting device 321 may be formed. The additional transparent area h' may be disposed adjacent to the light receiving sensor 311 in a direction of intersecting with the first and second green light emitting devices 312a and 312b.

That is, the light emitting devices are disposed to be spaced apart from each other by a predetermined distance based on the light receiving sensor. Hereinafter, the arrangement structures of the light receiving sensor and the light emitting devices will be described with reference to FIGS. 9A to 15D. The light receiving sensor and the light emitting sensors are individually fixed to the circuit board or the accommodating unit. The foregoing mounting structure is applied to arrangements of the light receiving sensor and the light emitting devices to be explained.

Figure 9A:
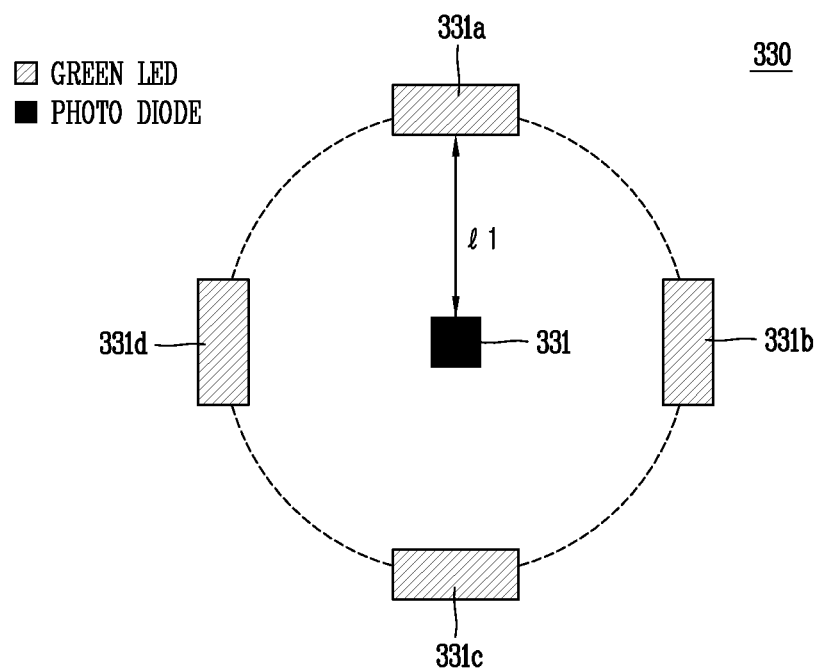
FIGS. 9A and 9B are conceptual views illustrating arrangement structures of one light emitting sensor and a plurality of light emitting devices.
Figure 9B:
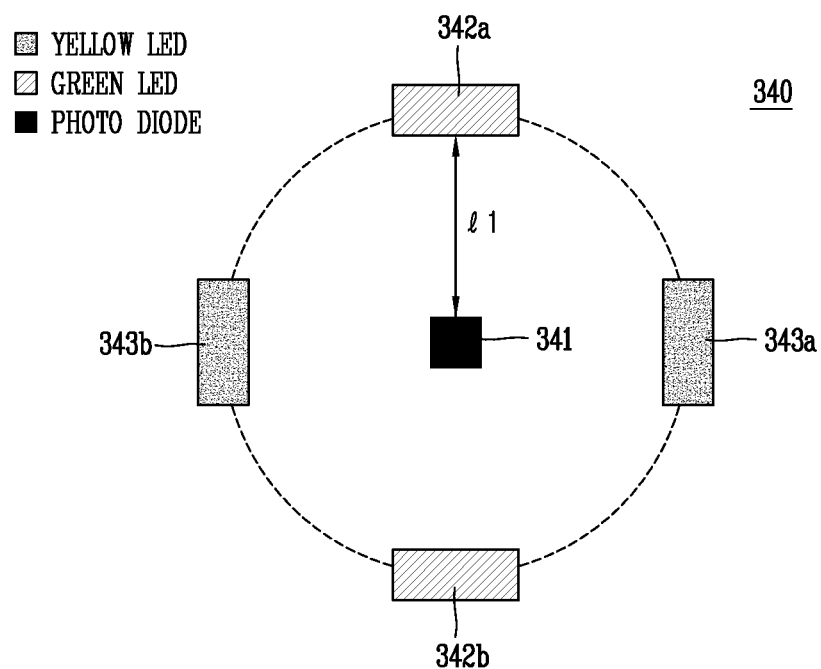

FIGS. 9A and 9B are conceptual views illustrating arrangement structures of one light emitting sensor and a plurality of light emitting devices.

A third sensing unit 330 according to FIG. 9A includes a light receiving sensor 331, and first to fourth green light emitting devices 331a, 331b, 331c and 331d. The first to fourth green light emitting devices 331a, 331b, 331c and 331d may be disposed to be the farthest away from one another based on the light receiving sensor 331.

One of the first to fourth green light emitting devices 331a, 331b, 331c and 331d may be implemented as an IR-integrated light emitting device which can output IR light. Each of the first to fourth green light emitting devices 331a, 331b, 331c and 331d is spaced apart from the light receiving sensor 331 by a first length l1. For example, the first length l1 may be in the range of about 3.0 mm to 4.0 mm.

A fourth sensing unit 340 according to FIG. 9B includes a light receiving sensor 341, first and second green light emitting devices 342a and 342b, and first and second yellow light emitting devices 343a and 343b. The plurality of light emitting devices may be arranged to be spaced apart from one another based on the light receiving sensor 341, and the first length l1 may be maintained between the light receiving sensor 341 and each of the light emitting devices.

The first and second green light emitting devices 342a and 342b are disposed to face each other, and the first and second yellow light emitting devices 343a and 343b are disposed to face each other.

Yellow light output from the first and second yellow light emitting devices 343a and 343b may be transmitted into a deeper area than green light. This may allow for collecting an accurate biometric signal even from a body with a thick skin or a body with a dark skin color, on the basis of the yellow light reaching up to the deeper area of the skin.

Figure 10A:
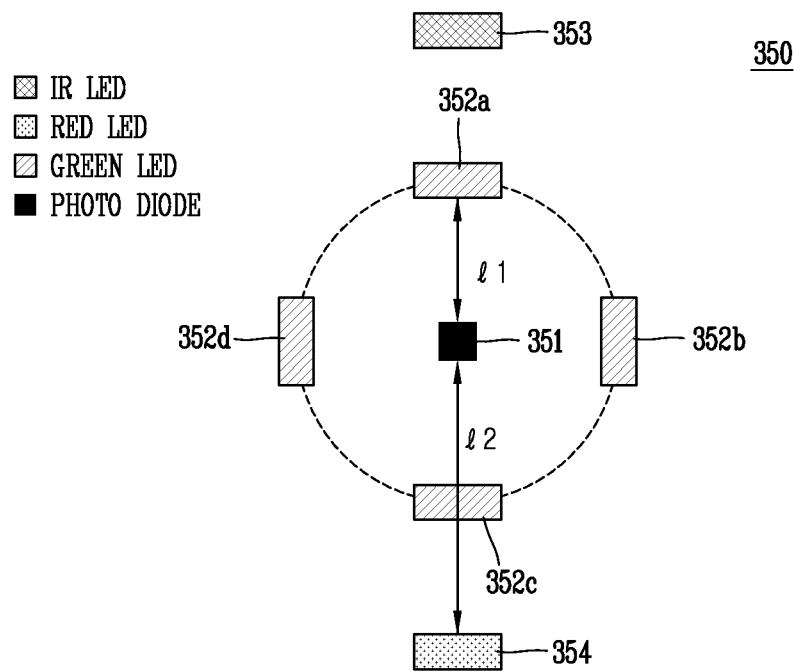
FIGS. 10A to 10O are conceptual views illustrating a sensing unit for outputting red light for measuring oxygen saturation.

FIGS. 10A to 10O are conceptual views illustrating a sensing unit for outputting red light for measuring oxygen saturation.

A fifth (5$^{th}$) sensing unit 350 according to FIG. 10A includes a light receiving sensor 351, first to fourth green light emitting devices 352a, 352b, 352c and 352d, and a red light emitting device 354.

Hemoglobin (Hb) and oxygen hemoglobin (HbO2) relatively well absorb IR light and red light, and exhibit different light absorbencies according to light wavelengths. That is, each of the hemoglobin (Hb) and the oxygen hemoglobin (HbO2) exhibits IR light absorbency and red light absorbency which are different from each other, and the absorbency of the hemoglobin and the absorbency of the oxygen hemoglobin are also differently measured.

Therefore, the controller 180 controls the IR sensor 353 and the red light emitting device 354 to output IR light and red light, respectively, and measures an amount of reflected light of each of the IR light and the red light. The controller 180 then measures IR light and red light absorbencies of the hemoglobin, and IR light and red light absorbencies of the oxygen hemoglobin according to the amounts of reflected light. The controller 180 may thus calculate oxygen saturation a rate of the oxygen hemoglobin (HbO2) to entire hemoglobin (Hb) (i.e., the sum of hemoglobin combined with oxygen and hemoglobin not combined with oxygen).

The first to fourth green light emitting devices 352a, 352b, 352c and 352d are spaced apart from one another by the first length l1, on the basis of the light receiving sensor 351. Meanwhile, the IR sensor 353 is disposed in parallel to the first green light emitting device 352a, and spaced apart from the light receiving sensor 351 by a second length l2 which is longer than the first length l1.

The red light emitting device 354 is disposed in parallel to the third green light emitting device 352c, and spaced apart from the light receiving sensor 351 by the second length l2. According to this embodiment, the IR sensor 353 and the red light emitting device 354 may be disposed at the farthest areas from each other. For example, the second length l2 may be in the range of about 6 mm to 8 mm.

Figure 10B:
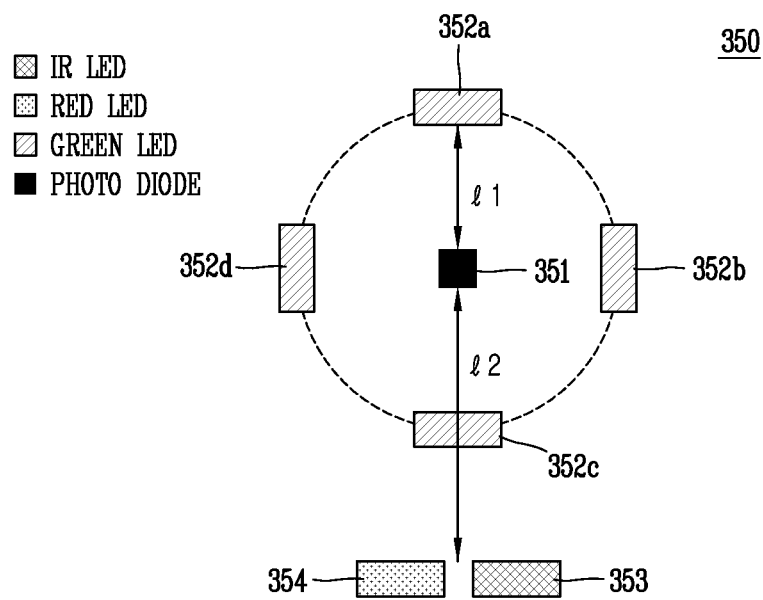

Referring to FIG. 10B, the IR sensor 353 and the red light emitting device 354 may be disposed adjacent to each other. According to this embodiment, the IR sensor 353 and the red light emitting device 354 may be disposed in series to each other, and spaced apart from the light receiving sensor 351 by the second length l2. The IR sensor 353 and the red light emitting device 354 may be disposed adjacent to one of the plurality of green light emitting devices.

Figure 10C:
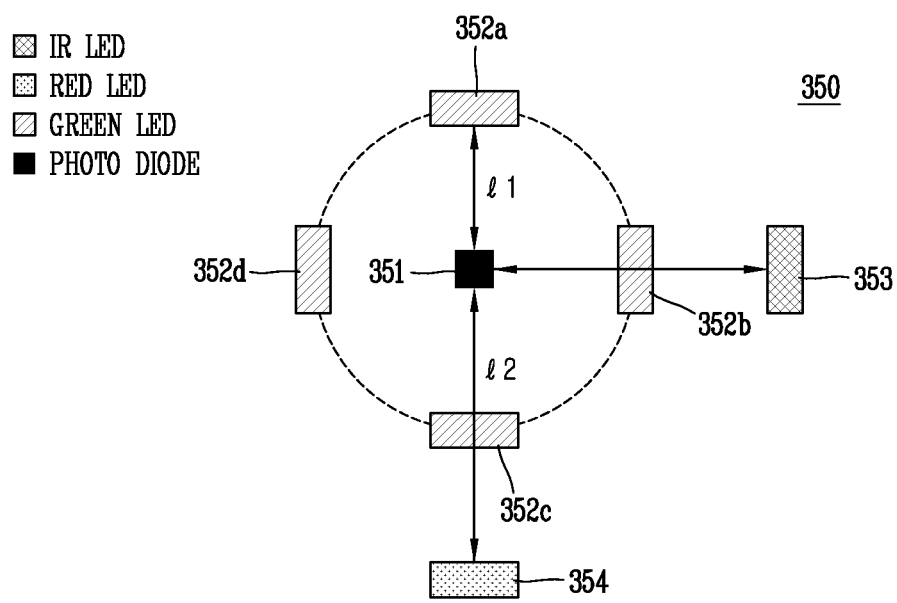

Referring to FIG. 10C, the IR sensor 353 and the red light emitting device 354 are disposed to be spaced apart from the first receiving sensor 351, respectively, by the second length l2. The IR sensor 353 may be adjacent to the second green light emitting device 352a, and the red light emitting device 354 may be adjacent to the third green light emitting device 352c.

According to these embodiments, biometric signals can be measured by adjusting output strength of the green light of the green light emitting devices to be appropriate for the user's skin, and the oxygen saturation can be measured by using the red light. Also, whether or not the watch type terminal has been worn can be detected through the IR sensor.

FIGS. 11A to 11E are conceptual views illustrating a sixth (6$^{th}$) sensing unit including green light emitting devices, a red light emitting device and a yellow light emitting device.

Figure 11A:
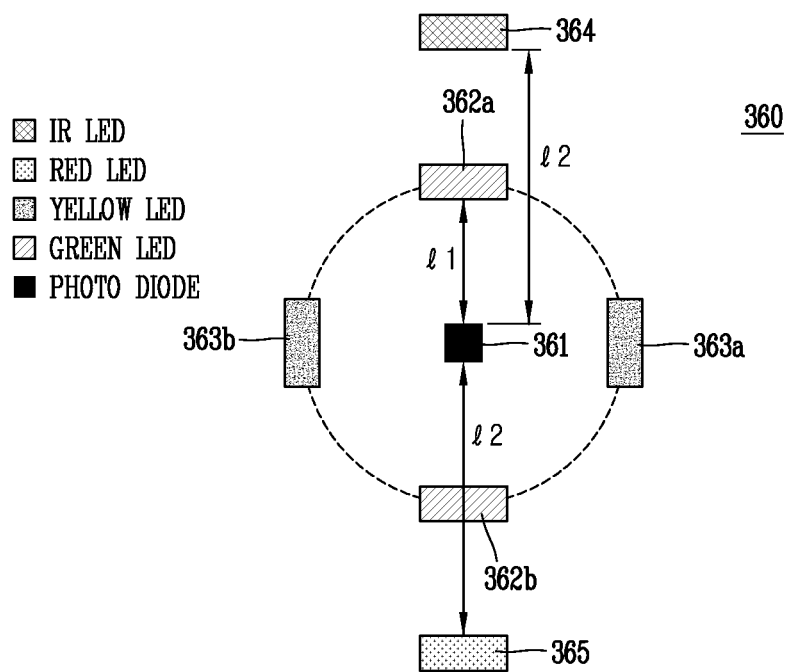
FIGS. 11A to 11E are conceptual views illustrating a sixth sensing unit including green light emitting devices, a red light emitting device and yellow light emitting devices.

Referring to FIGS. 11A to 11O, on the basis of a light receiving sensor 361, first and second green light emitting devices 362a and 362b are disposed to face each other and first and second yellow light emitting devices 363a and 363b are disposed to face each other. The first and second green light emitting devices 362a and 362b and the first and second yellow light emitting devices 363a and 363b are spaced apart from the light receiving sensor 361, respectively, by the first length l1.

As illustrated in FIG. 11A, a red light emitting device 365 is disposed adjacent to the second green light emitting device 362b, and an IR sensor 364 is disposed adjacent to the first green light emitting device 362a. The red light emitting device 365 and the IR sensor 364 are spaced apart from the light receiving sensor 361, respectively, by a second length l2.

Figure 11B:
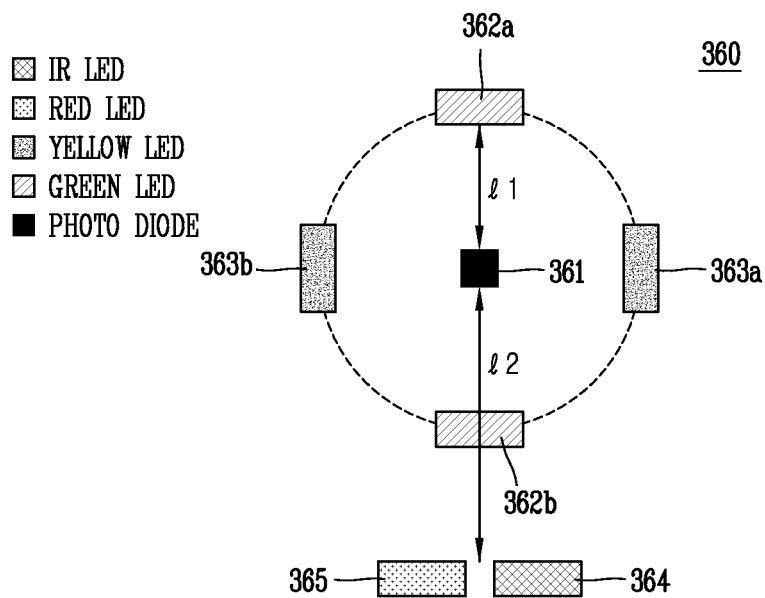

Meanwhile, as illustrated in FIG. 11B, the red light emitting device 365 and the IR sensor 364 may be disposed adjacent to each other. The red light emitting device 365 and the IR sensor 364 are disposed adjacent to a green light emitting device (e.g., 362b).

Figure 11C:
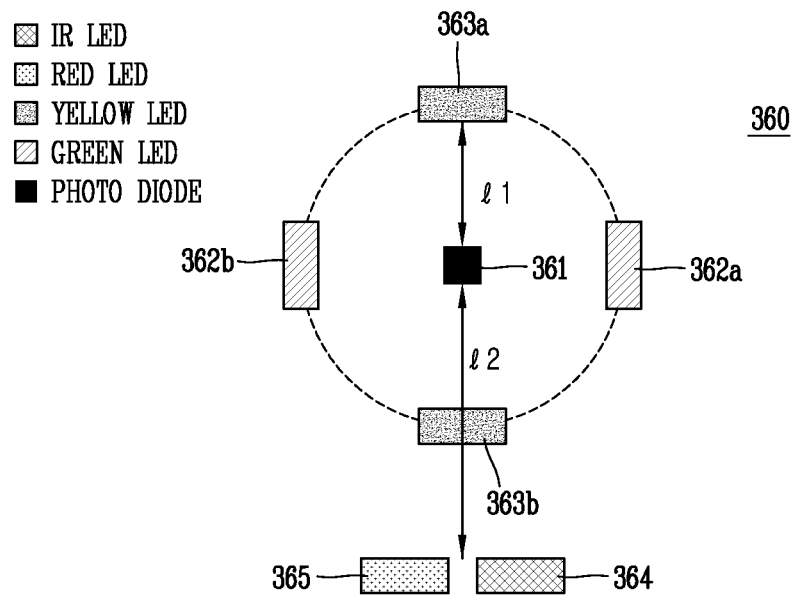

Referring to FIG. 11C, the red light emitting device 365 and the IR sensor 364 are disposed adjacent to each other, and both disposed adjacent to a yellow light emitting device (e.g., 363b).

Figure 11D:
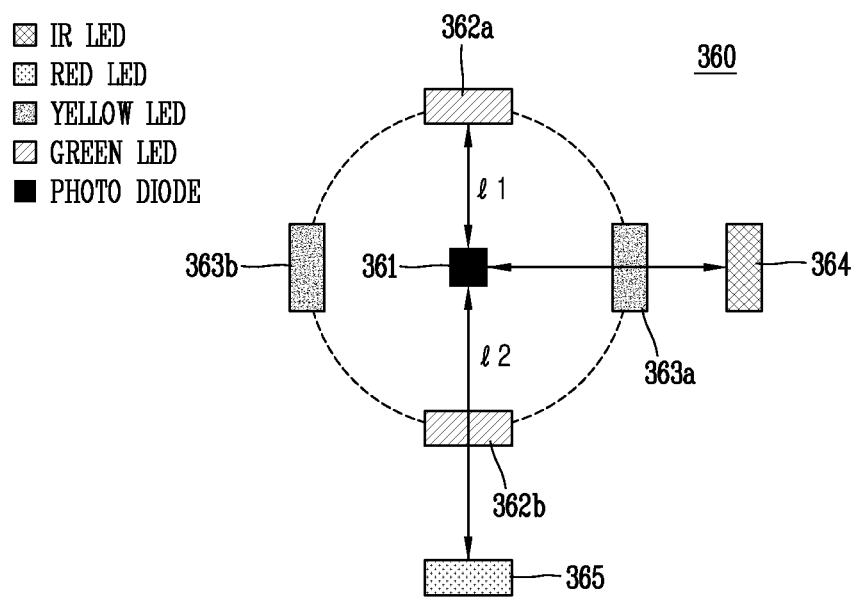
Figure 11E:
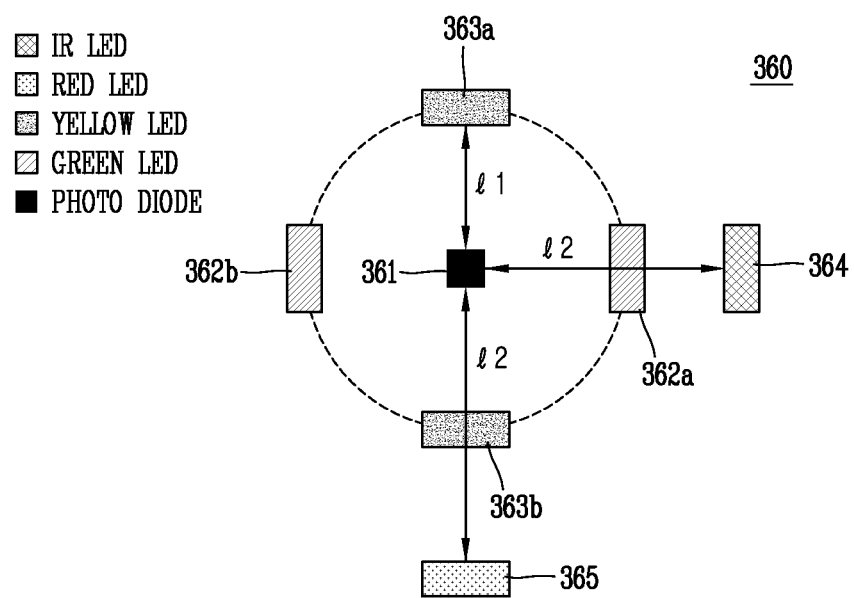

Referring to FIGS. 11D and 11E, the red light emitting device 365 and the IR sensor 364 are disposed adjacent to a green light emitting device (e.g., 362b) and a yellow light emitting device (e.g., 363a), respectively.

Figure 12A:
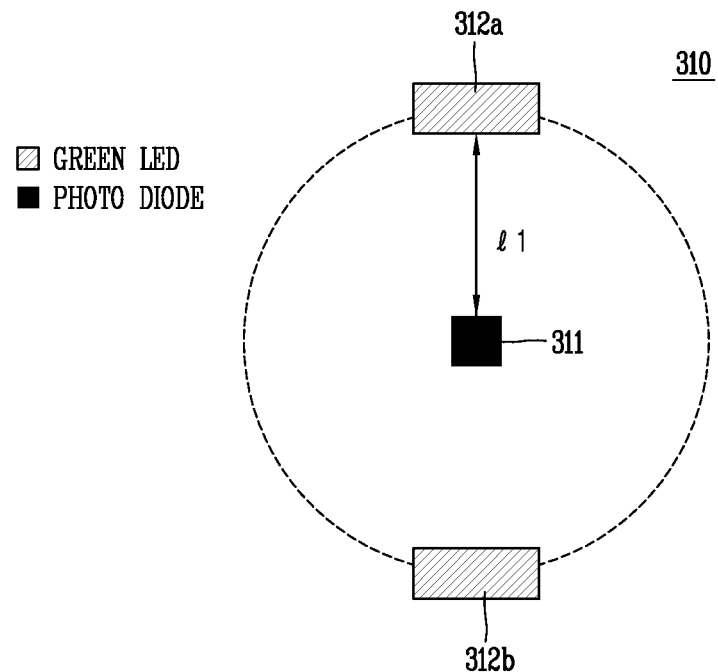
FIGS. 12A and 12B are conceptual views illustrating a sensing unit in accordance with one exemplary embodiment.
Figure 12B:
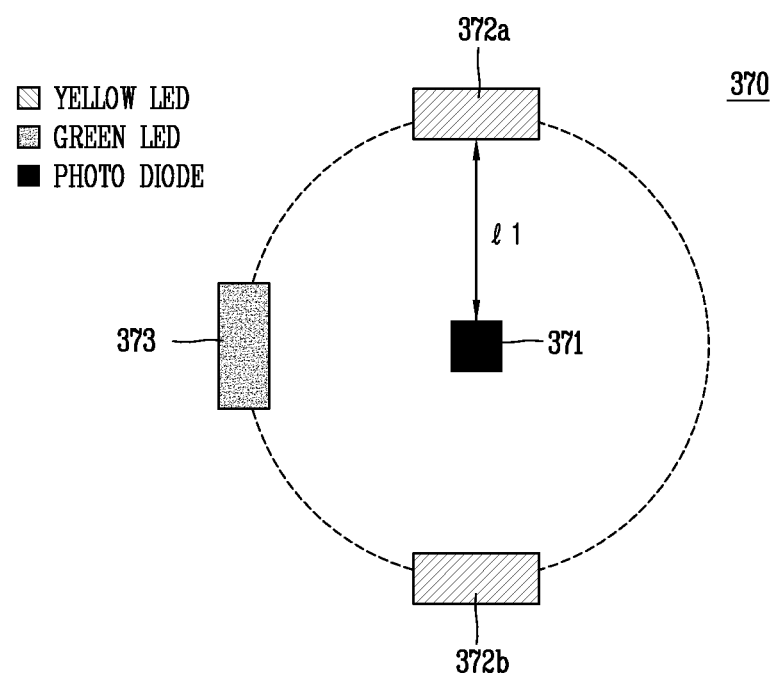

FIGS. 12A and 12B are conceptual views illustrating a sensing unit in accordance with one exemplary embodiment.

FIG. 12A illustrates a first sensing unit 310 which includes first and second green light emitting devices 312a and 312b disposed to face each other with interposing a light receiving sensor 311 therebetween.

FIG. 12B illustrates a seventh (7$^{th}$) sensing unit 370 which includes first and second green light emitting devices 372a and 372b arranged to face each other with interposing a light receiving sensor 371 therebetween, and a yellow light emitting device 373. The yellow light emitting device 373 may be an IR-integrated LED outputting IR light.

FIGS. 13A to 13D are conceptual views illustrating an eighth (8$^{th}$) sensing unit including a light receiving sensor, green light emitting devices, a yellow light emitting device, a red light emitting device and an IR sensor.

Figure 13A:
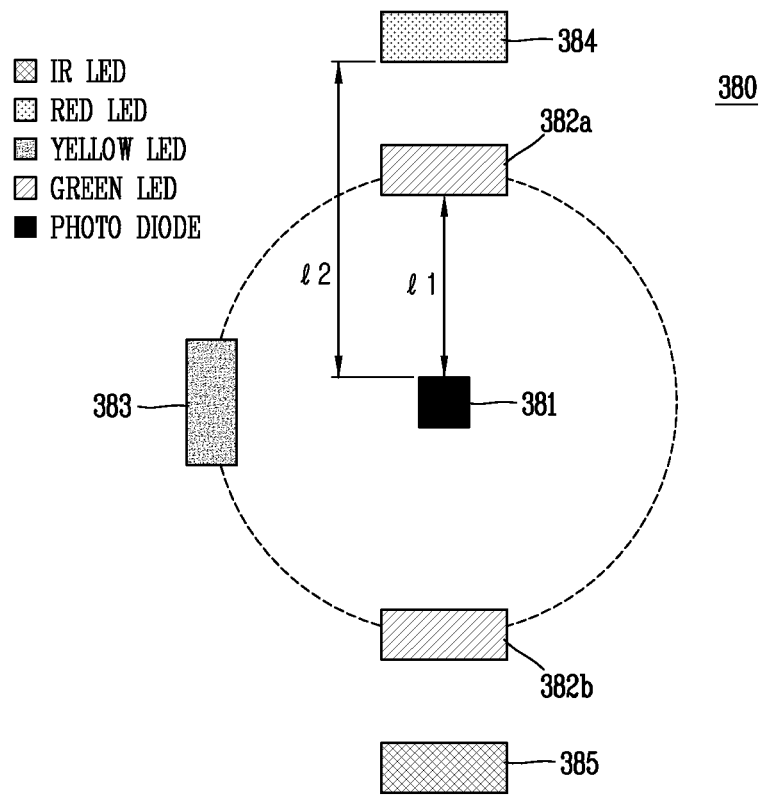
FIGS. 13A to 13D are conceptual views illustrating an eighth sensing unit including a light receiving sensor, a green light emitting device, an yellow light emitting device, a red light emitting device and an IR sensor.

As illustrated in FIG. 13A, first and second green light emitting devices 382a and 382b are disposed to face each other in a manner of being spaced apart from a light receiving sensor 381 by a first length l1, respectively, and a yellow light emitting device 383 is additionally disposed. An IR sensor 385 and a red light emitting device 384 are disposed in parallel to the first and second green light emitting devices 382a and 382b, and spaced apart from the light receiving sensor 381, respectively, by a second length l2.

Figure 13B:
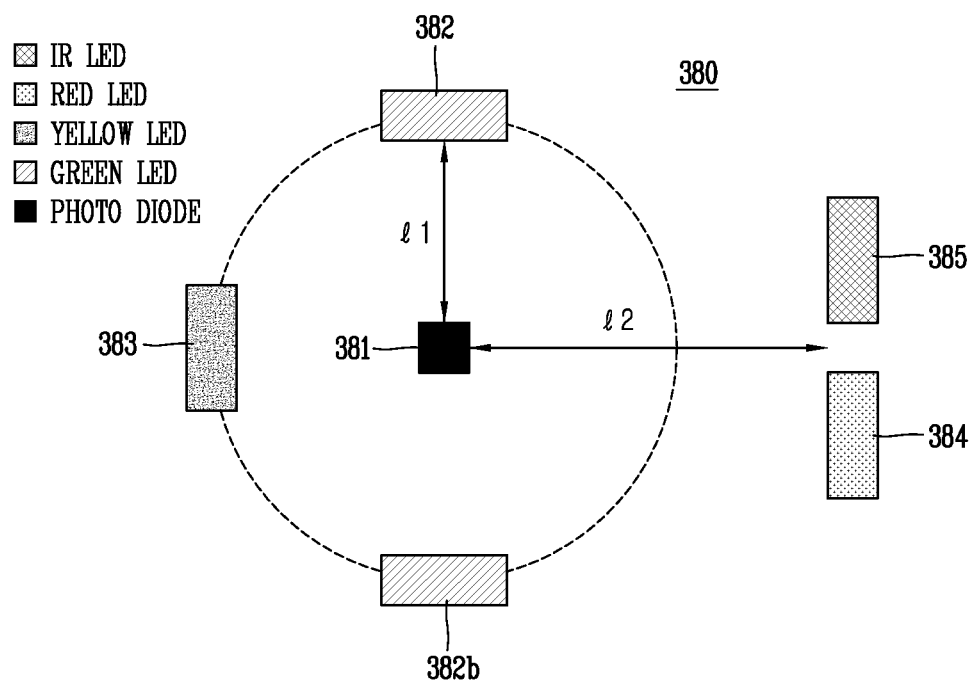

Referring to FIG. 13B, the IR sensor 385 and the red light emitting device 384 are disposed adjacent to each other, and face the yellow light emitting device 383 with interposing the light receiving sensor 381 therebetween. In this instance, the yellow light emitting device 383 may alternatively be disposed adjacent to the red light emitting device 384.

Figure 13C:
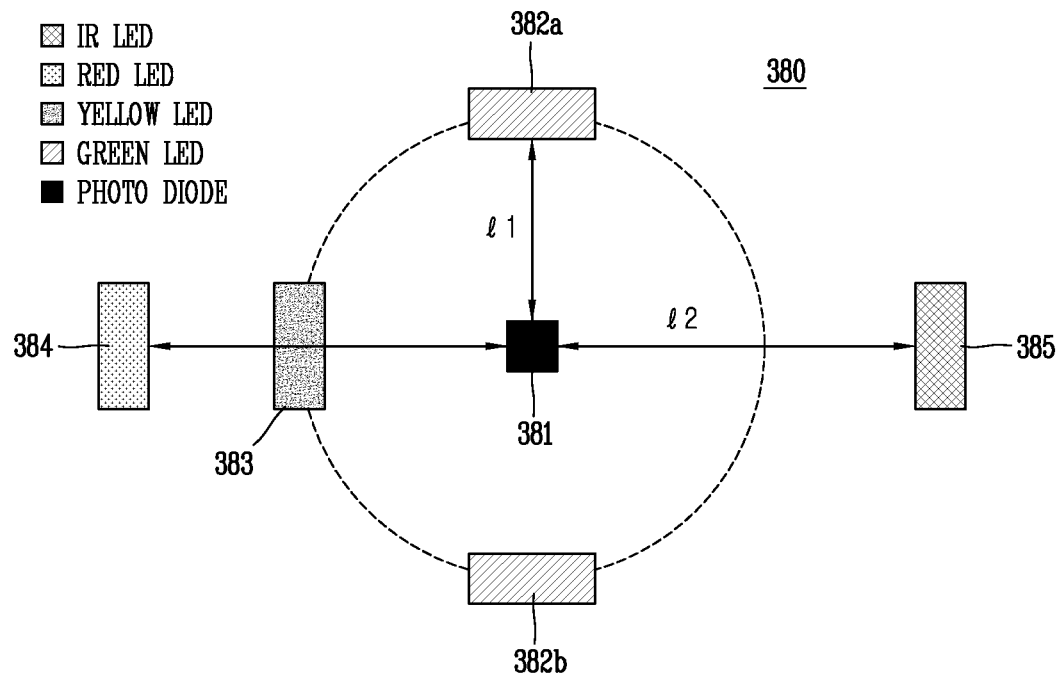

Referring to FIG. 13C, the light receiving sensor 381, the IR sensor 385 and the red light emitting device 384 may be arranged in one direction, and the red light emitting device 384 and the yellow light emitting device 383 may be disposed adjacent to each other.

In this instance, the yellow light emitting device 383 may alternatively be disposed adjacent to the IR sensor 385.

Figure 13D:
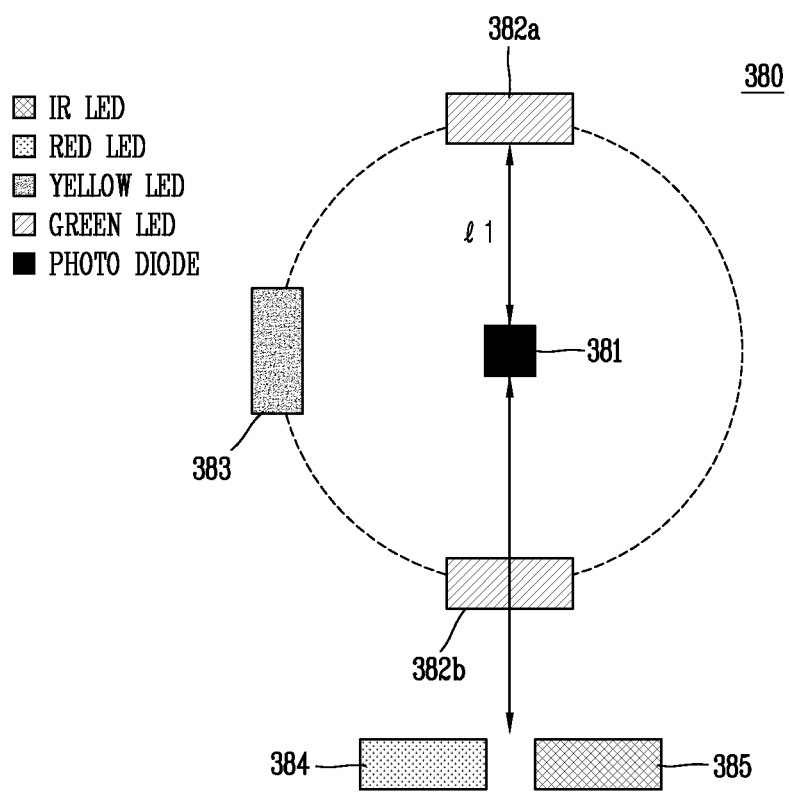

The eighth sensing unit 380 according to FIG. 13D has a structure in which the IR sensor 385 and the red light emitting device 384 are disposed adjacent to each other, and one of the first and second green light emitting devices 382a and 382b which face each other is adjacent to the IR sensor 385 and the red light emitting device 384.

Figure 14A:
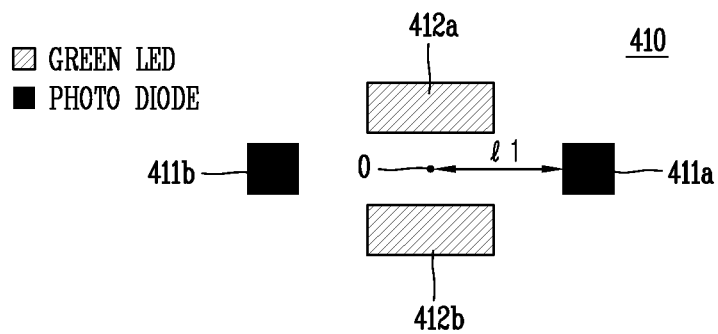
FIGS. 14A to 14C are conceptual views illustrating a sensing unit including two light receiving sensors.
Figure 14B:
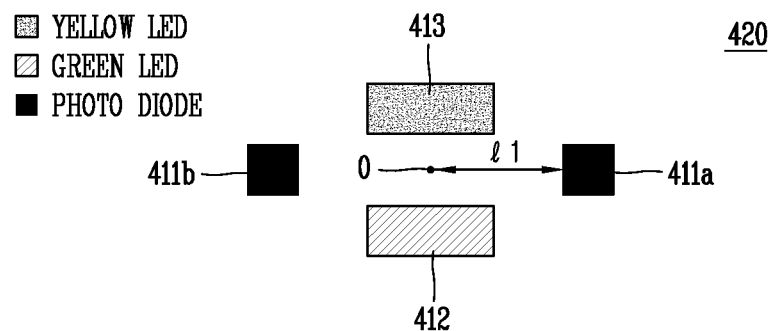

FIGS. 14A and 14B are conceptual views illustrating a sensing unit including two light receiving sensors.

According to this embodiment, a ninth (9$^{th}$) sensing unit 410 includes first and second light receiving sensors 411a and 411b which are spaced apart from each other based on a virtual center O. For example, the first and second light receiving sensors 411a and 411b may be spaced apart from each other by the first length l1 based on the center O. The first and second light receiving sensors 411a and 411b are disposed in a first direction.

When the first and second light receiving sensors 411a and 411b are disposed in the first direction, first and second green light emitting devices 412a and 412b are spaced apart from each other in a second direction which intersects with the first direction.

Referring to FIG. 14B, a tenth (10$^{th}$) sensing unit 420 includes first and second light receiving sensors 411a and 411b disposed in the first direction, and a green light emitting device 412 and a yellow light emitting device 413 disposed in the second direction.

Figure 14C:
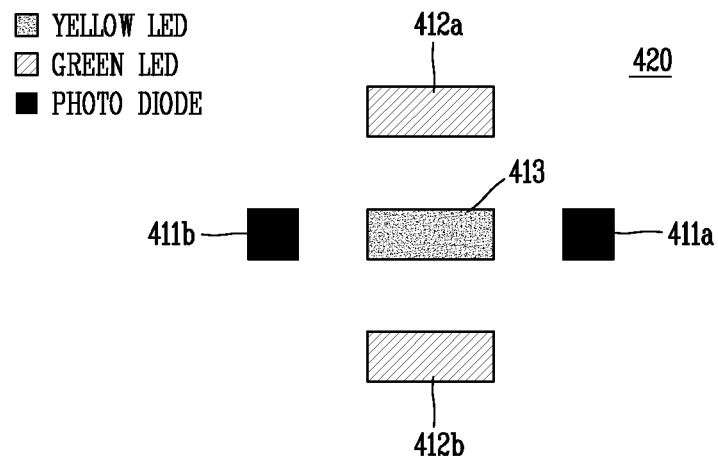

FIG. 14C includes first and second green light emitting devices 412a and 412b arranged in the second direction, and a yellow light emitting device 413 disposed between the first and second green light emitting devices 412a and 412b.

In this instance, the yellow light emitting device or the green light emitting device may be implemented as an IR-integrated LED.

FIGS. 15A to 15D are conceptual views illustrating an eleventh (11$^{th}$) sensing unit 430 including two green light emitting devices, two light receiving sensors, a red light emitting device and an IR sensor.

Figure 15A:
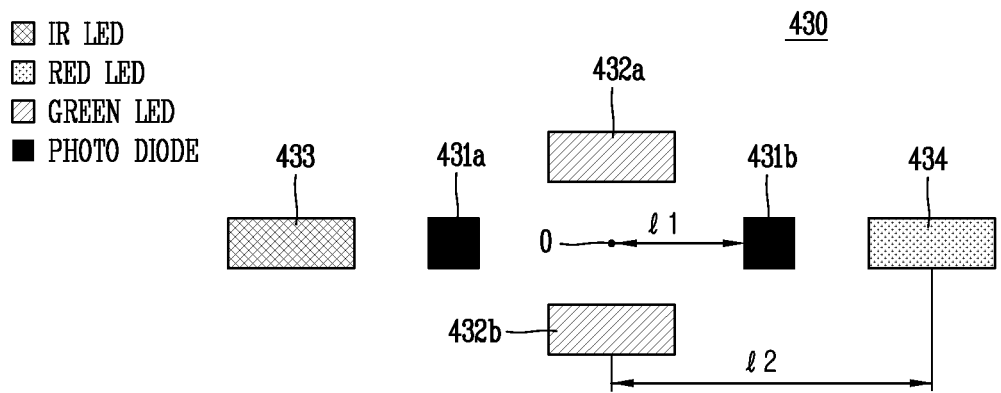
FIGS. 15A to 15D are conceptual views illustrating an eleventh sensing unit including two green light emitting devices, two light receiving sensors, a red light emitting device and an IR sensor.

Referring to FIG. 15A, first and second light receiving sensors 431a and 431b are arranged in the first direction on the basis of a virtual center O. Each of the first and second light receiving sensors 431a and 431b are spaced apart from the center O by the first length l1.

An IR sensor 433 and a red light emitting device 434 are arranged along the first direction, and spaced apart from the center O, respectively, by the second length l2.

Meanwhile, the first and second green light emitting devices 432a and 432b are arranged in the second direction intersecting with the first direction.

Figure 15B:
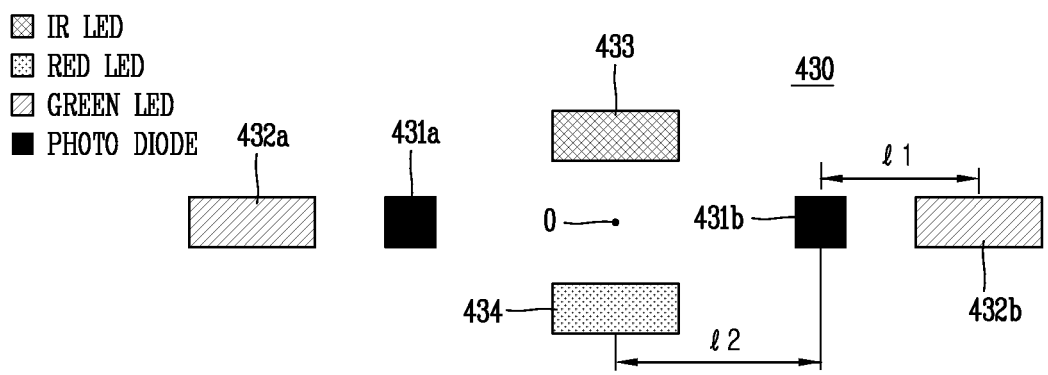

On the other hand, referring to FIG. 15B, the first and second green light emitting devices 432a and 432b and the first and second light receiving sensors 431a and 431b are arranged in the first direction. The first and second light receiving sensors 431a and 431b are spaced apart from the virtual center O by the second length l2. The first and second green light emitting devices 432a and 432b are spaced from the first and second light receiving sensors 431a and 432b, respectively, by the first length l1, and disposed more outside than the first and second light receiving sensors 431a and 431b.

The IR sensor 433 and the red light emitting devices 434 are arranged in the second direction intersecting with the first direction.

Figure 15C:
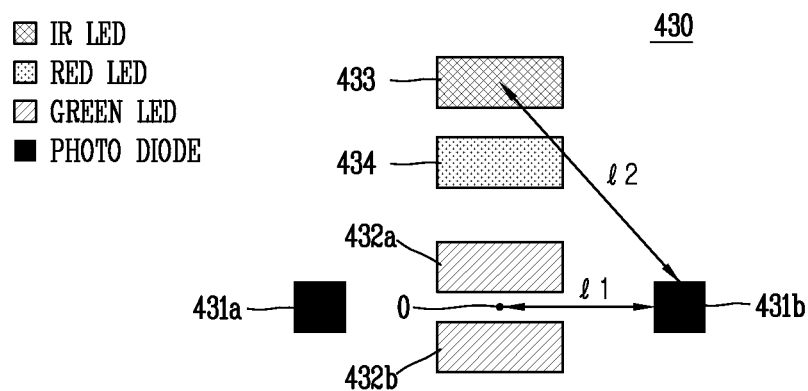

Referring to FIG. 15C, the first and second green light emitting devices 432a and 432b, the red light emitting device 434 and the IR sensor 433 are arranged in one direction on the basis of the center O. The first and second light receiving sensors 431a and 431b are arranged in a direction intersecting with the one direction on the basis of the center O. The first and second light receiving sensors 431a and 431b are disposed to be close to the first and second green light emitting devices 432a and 432b, and relatively far away from the IR sensor 433 and the red light emitting device 434. The first and second light receiving sensors 431a and 431b and the IR sensor 433 are preferably spaced apart from each other by the second length l2.

Figure 15D:
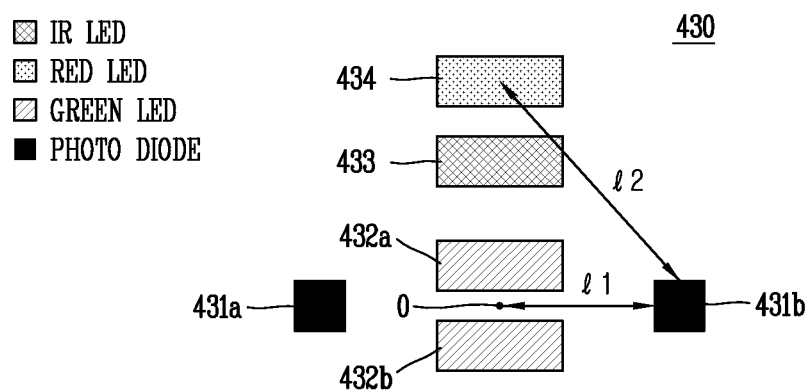

As illustrated in FIG. 15D, the positions of the IR sensor 433 and the red light emitting device 434 may be switched with each other.

Figure 16A:
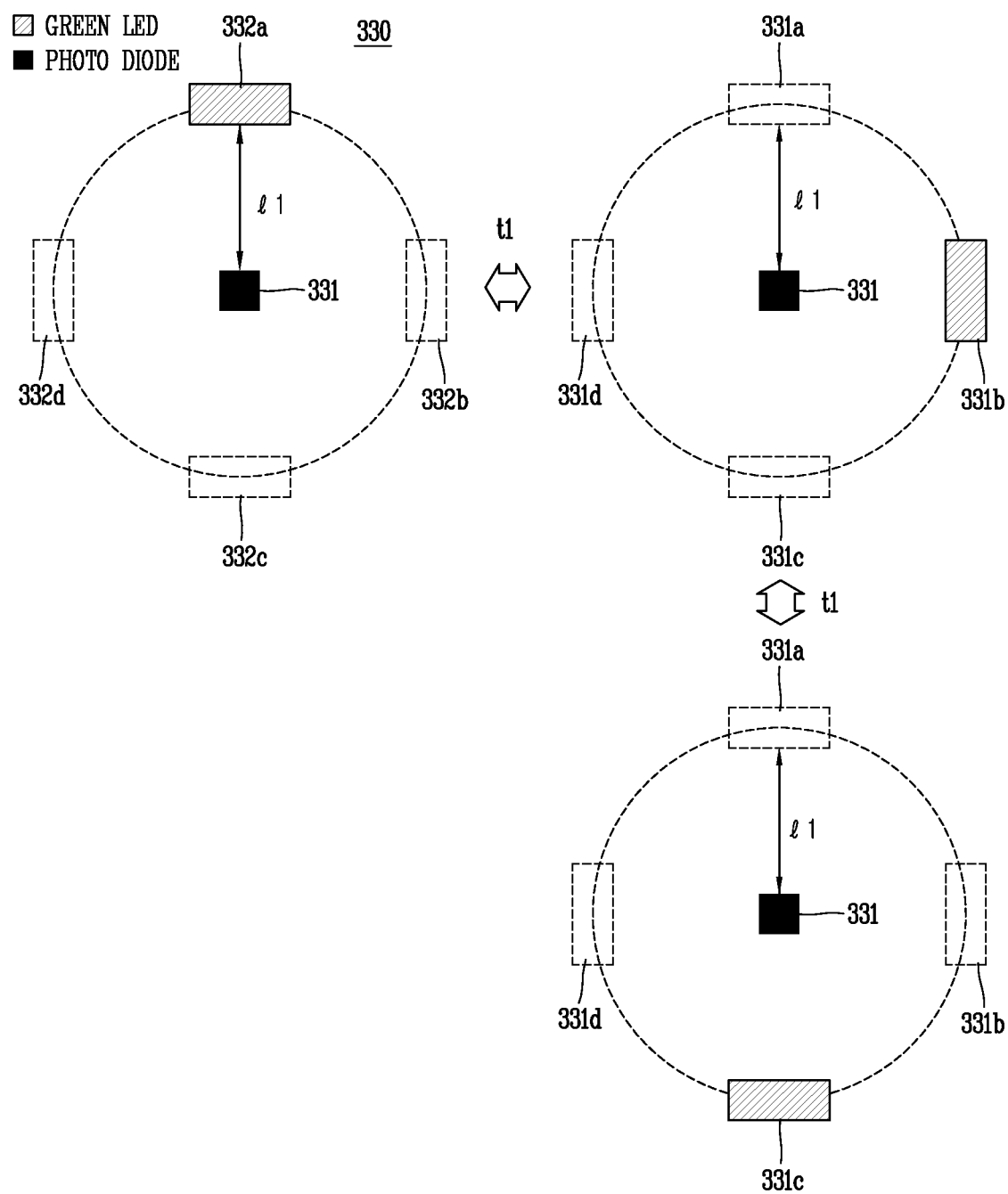
FIGS. 16A and 16B are conceptual views illustrating a method of controlling an output of a light emitting device.
Figure 16B:
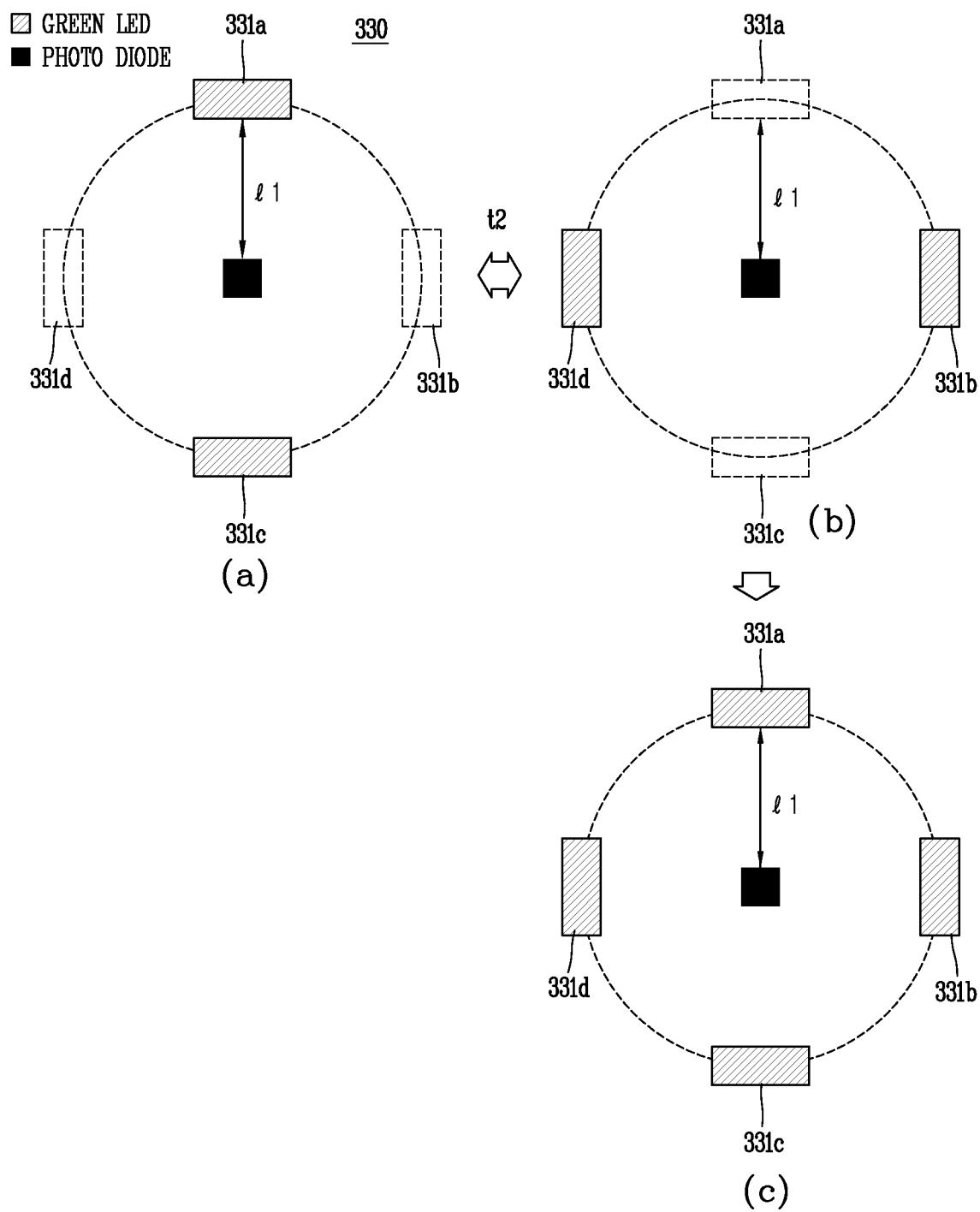

FIGS. 16A and 16B are conceptual views illustrating a method of controlling an output of a light emitting device.

FIG. 16A illustrates a third sensing unit 330 which includes first to fourth green light emitting devices 332a, 332b, 332c and 332d disposed to surround a light receiving sensor 331.

The controller 180 outputs green light by activating one of the first to fourth green light emitting devices 332a, 332b, 332c and 332d when a specific command or wearing of the watch type terminal is detected.

The watch type terminal 100 according to this embodiment includes at least one sensing unit for detecting a movement, and controls the output of the plurality of green light emitting devices based on a degree of the movement detected by the sensing unit.

For example, when it is determined that a movement detected by the sensing unit is a first level (rarely moved), the controller 180 controls the third sensing unit 330 to output green light through the four green light emitting devices one by one in an alternating manner. The order of activating the plurality of green light emitting devices may not be limited to that illustrated in the drawing.

The controller 180 controls one of the plurality of green light emitting devices to output green light per a preset first time t1. For example, the first time t1 may correspond to 3 minutes.

Meanwhile, referring to FIG. 16B, when it is detected through the sensing unit that the movement of the watch type terminal 100 corresponds to a second level higher than the first level, the controller 180 controls the third sensing unit 330 to simultaneously turn off and on two of the four green light emitting devices. The controller 180 controls two green light emitting devices facing each other to be simultaneously activated (e.g., the first and third green light emitting devices 332a and 332c are simultaneously turned on and the second and fourth green light emitting devices 332b and 332d are simultaneously turned on).

The controller 180 may control the two green light emitting devices to be turned on per a second time t2 (e.g., 30 seconds) faster than the first time t1.

The controller 180 may control the third sensing unit 330 to continuously activate the plurality of green light emitting devices when a movement of a third level is detected through the sensing unit.

According to this embodiment, when an accurate measurement is difficult due to the user's frequent movement, a quantity of light can be increased to increase a quantity of green light that reaches a blood vessel. Also, when a less movement is detected, a biometric signal can be collected by using a small amount of green light, which may result in a reduction of power consumption.

Figure 17A:
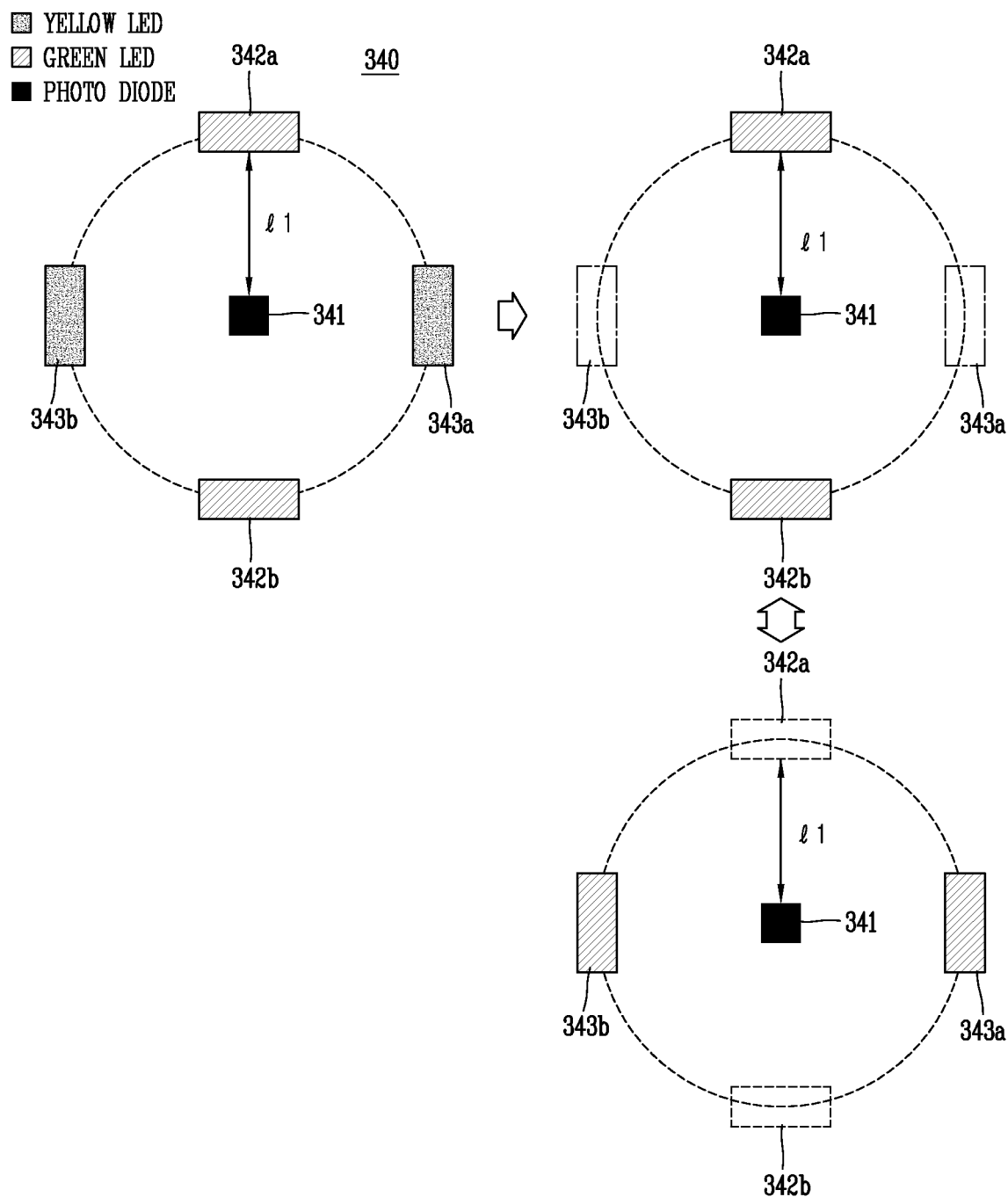
FIGS. 17A to 17C are conceptual views illustrating a control method of collecting a biometric signal from a thick skin using yellow light.
Figure 17B:
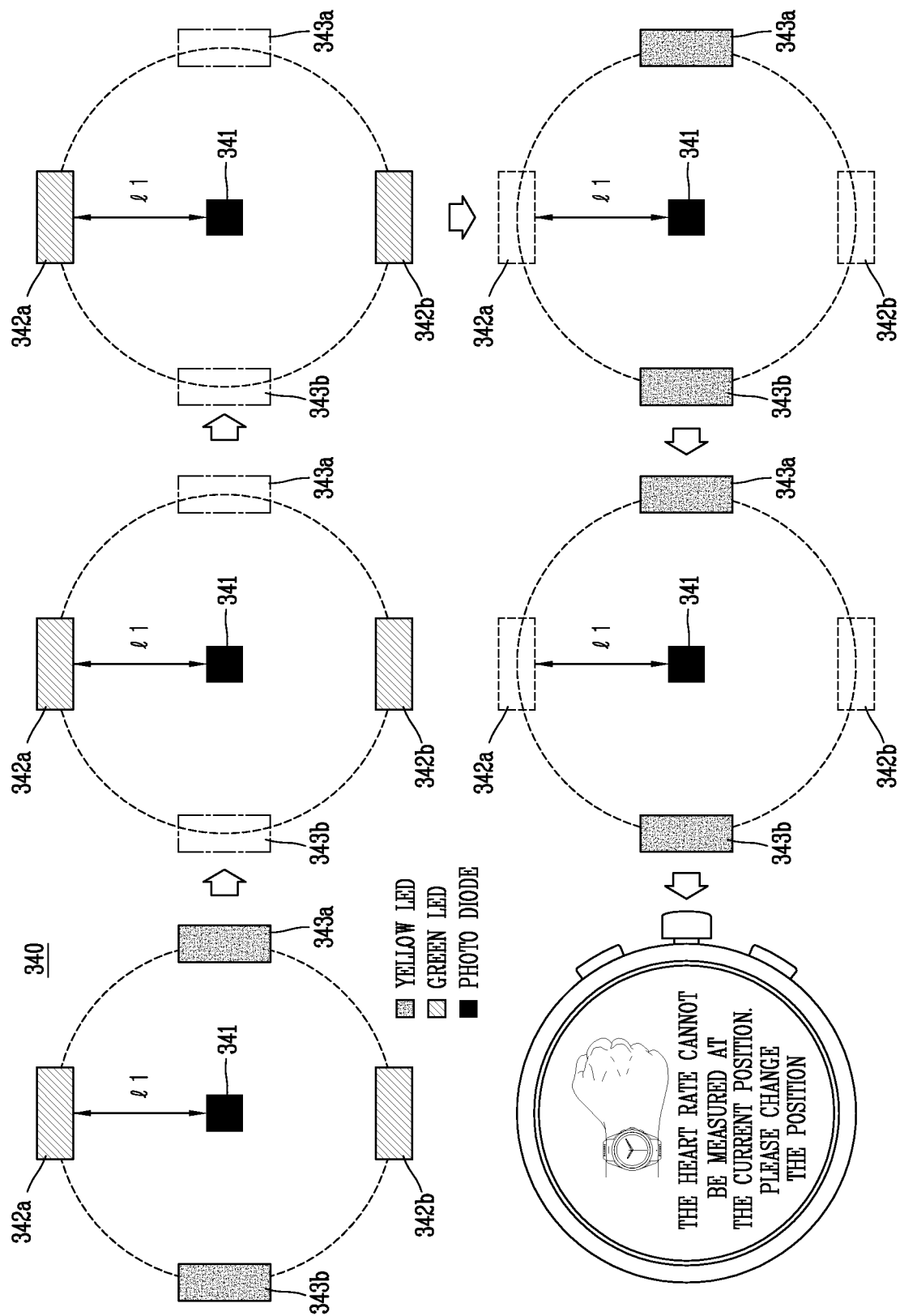
Figure 17C:
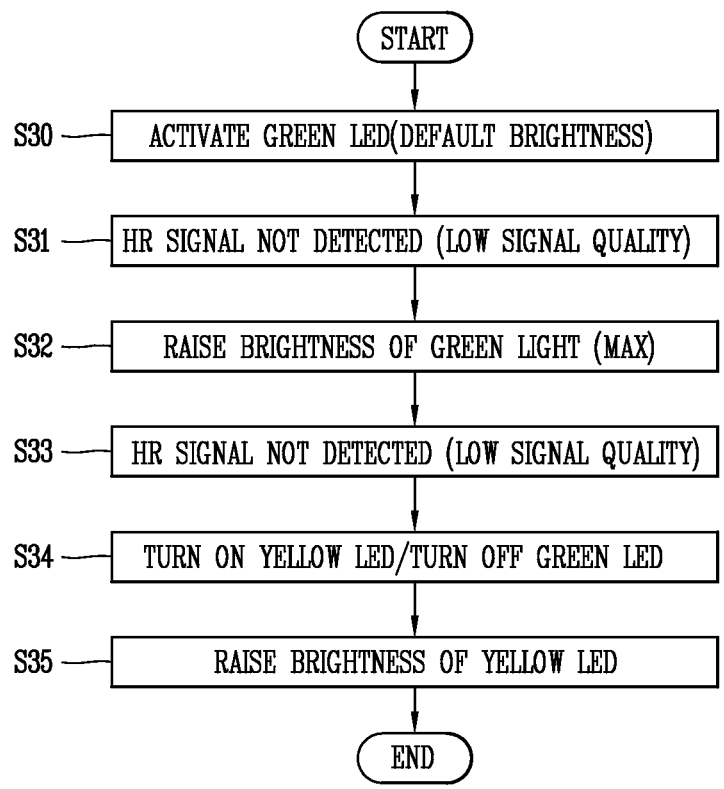

FIGS. 17A to 17C are conceptual views illustrating a control method of collecting a biometric signal from a thick skin using yellow light.

A fourth sensing unit 340 according to this embodiment includes first and second green light emitting devices 342a and 342b and first and second yellow light emitting devices 343a and 343b disposed to surround a light receiving sensor 341. The first and second green light emitting devices 342a and 342b face each other and the first and second yellow light emitting devices 343a and 343b face each other.

The controller 180 outputs green light using the first and second green light emitting devices 342a and 342b while the first and second yellow light emitting devices 343a and 343b are deactivated. When a biometric signal collected using the green light is within a normal range, the controller 180 collects biometric signals continuously using the first and second green light emitting devices 342a and 342b.

However, when the biometric signal collected using the first and second green light emitting devices 342a and 342b are not in the normal range, the controller 180 converts the first and second green light emitting devices 342a and 342b into an inactive state, and outputs yellow light using the first and second yellow light emitting devices 343a and 343b. The controller 180 determines whether or not a biometric signal collected using the first and second yellow light emitting devices 343a and 343b is in a normal range.

The controller 180 can selectively output the green light or the yellow light, so as to continuously collect the biometric signals by outputting light acquiring a biometric signal in the normal range.

In general, biometric signals within a normal range are collected using green light for skin colors of Asian, the white race and Indian, and using yellow light for African and a body of a person whose blood vessels are located deep in the body.

Accordingly, the present invention can collect more accurate biometric signals, irrespective of a skin color of a user wearing the watch type terminal 100.

Referring to FIGS. 17B and 17C, the controller 180 initially controls the first and second green light emitting devices 342a and 342b to output a first quantity of green light (or green light with first brightness (default brightness)) (S30). When a heart rate (HR) signal is not detected (low signal quality) (S31), the controller 180 may raise the brightness (quantity) of the green light to second brightness (or second quantity of light) (S32).

In this instance, the brightness may be set to be increased sequentially or directly to the maximum value.

When the heart rate (HR) signal is not detected (low signal quality) while the green light is output with the second brightness (S33), the controller deactivates the first and second green light emitting devices 342a and 342b, and activates the first and second yellow light emitting devices 343a and 343b so as to output yellow light (S34).

Also, the controller 180 may determine whether or not the heart rate (HR) signal is detected and increase the quantity of the yellow light (S35).

Referring to FIG. 17B, when the heart rate (HR) signal is within an abnormal range after outputting the greatest quantity of yellow light (i.e., outputting the yellow light with the highest brightness), the controller 180 may control the display unit 151 to output a guide screen for the user to change a wearing position of the watch type terminal 100.

Figure 18:
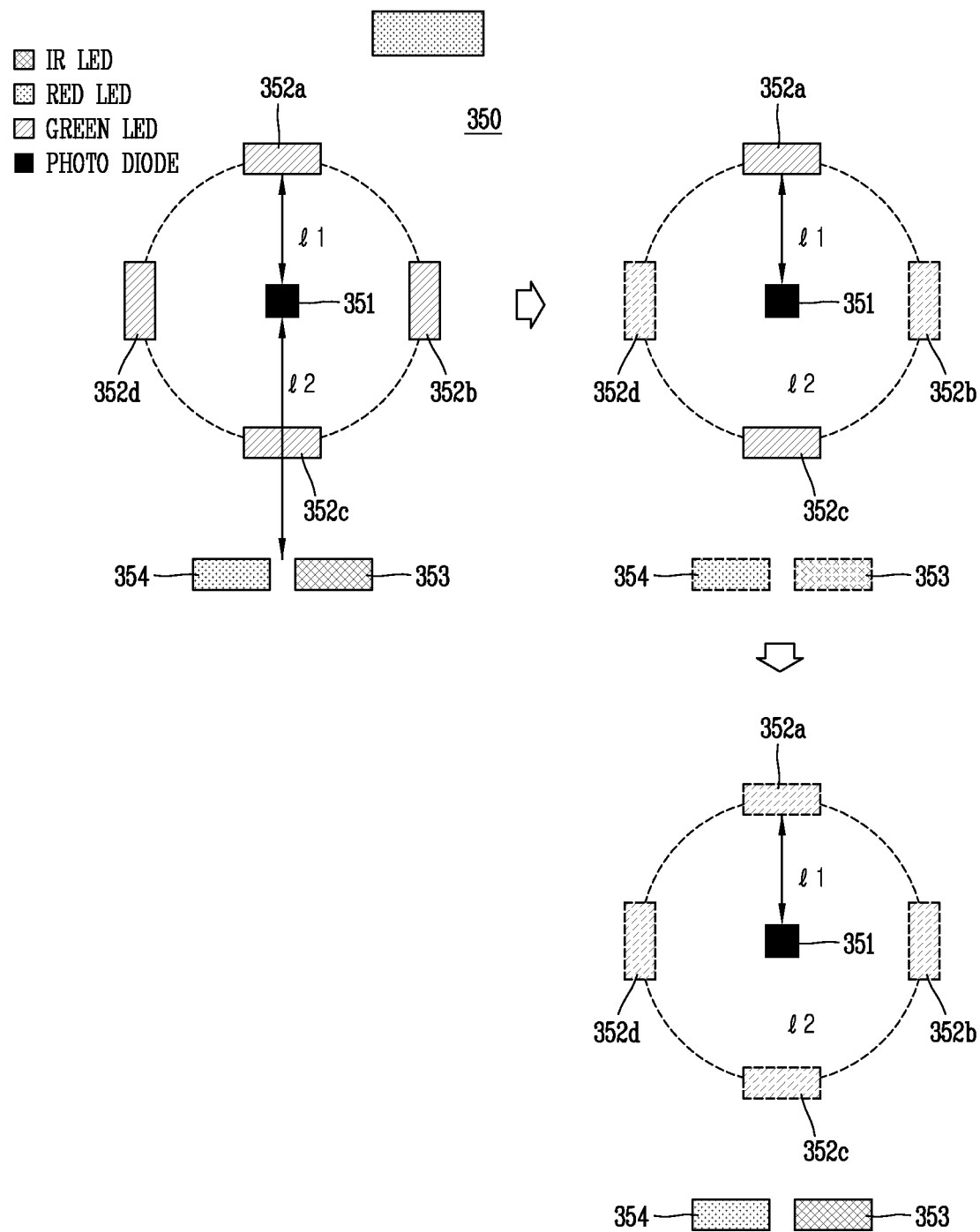
FIG. 18 is a conceptual view illustrating a control method of measuring oxygen saturation in a sleep mode.

FIG. 18 is a conceptual view illustrating a control method of measuring oxygen saturation in a sleep mode.

A fifth sensing unit 350 according to FIG. 18 includes first to fourth green light emitting devices 352a, 352b, 352c and 352d, an IR sensor 353 and a red light emitting device 354. When the sleep mode is activated, the controller 180 switches the first to fourth green light emitting devices 352a, 352b, 352c and 352d into an inactive state. Accordingly, the controller 180 merely activates the IR sensor 353 and the red light emitting device 354 to measure oxygen saturation.

Meanwhile, while activating at least part of the first to fourth green light emitting devices 352a, 352b, 352c and 352d to measure a biometric signal (pulsation information), the controller 180 deactivates the IR sensor 353 and the red light emitting device 354.

According to this embodiment, while measuring one kind of biometric signal, a type of light associated with the measurement can be output, thereby minimizing noise and acquiring an accurate measurement result.

Figure 19:
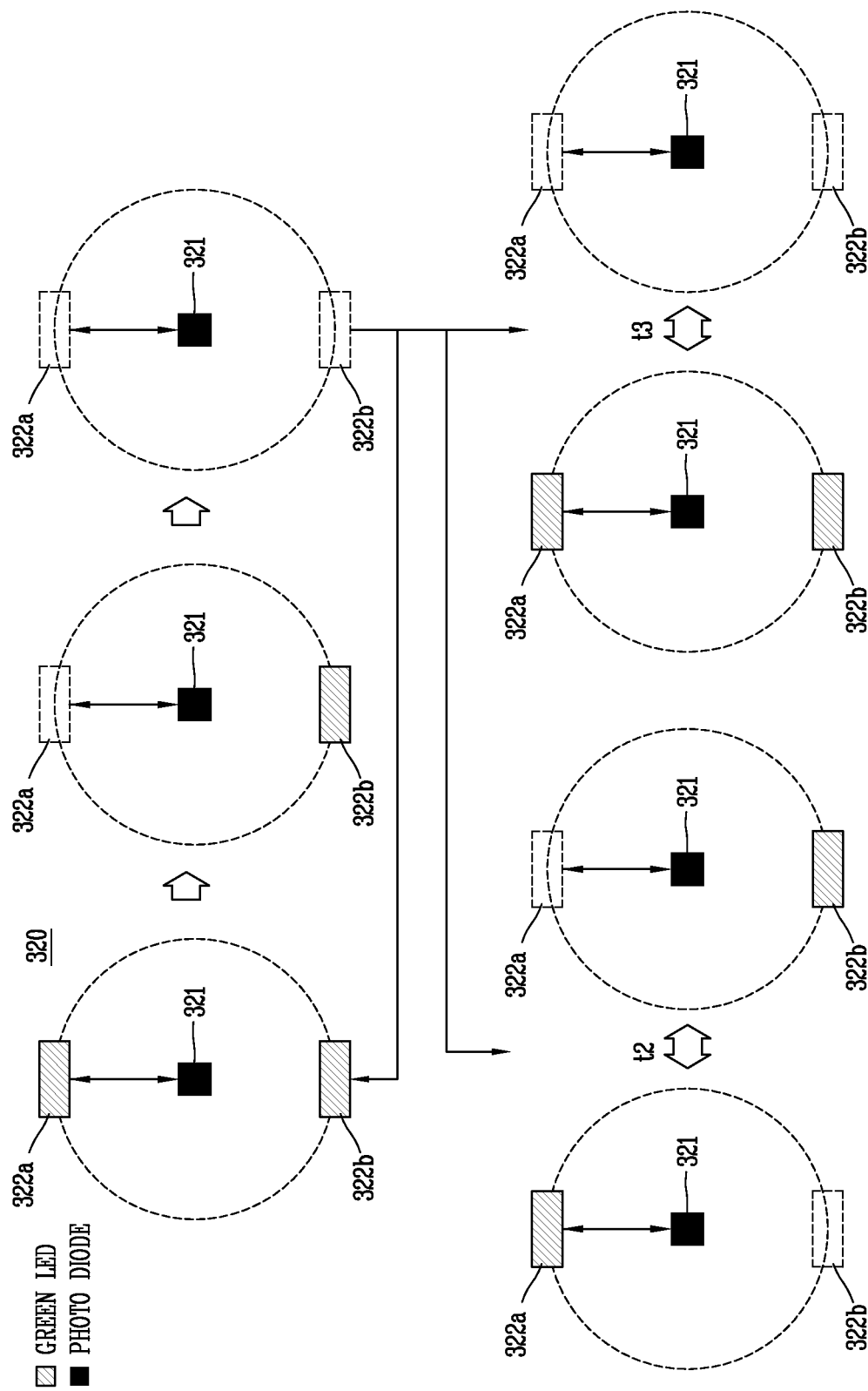
FIG. 19 is a conceptual view illustrating a control method of activating a plurality of green light emitting devices based on a motion.

FIG. 19 is a conceptual view illustrating a control method of activating a plurality of green light emitting devices based on a motion.

For example, FIG. 19 illustrates a second sensing unit 320 including first and second green light emitting devices 322a and 322b, and a light receiving sensor 321. The controller 180 detects a movement of the watch type terminal 100 while the first and second green light emitting devices 332a and 332b are in an active state.

When a less movement is detected, the controller 180 activates the plurality of green light emitting devices one by one in an alternating manner. On the other hand, when a great movement of the watch type terminal 100 is detected, the controller 180 controls the second sensing unit 320 to turn on/off the plurality of green light emitting devices at once.

That is, the controller 180 can adjust a number of light emitting devices activated and an output time of green light on the basis of a degree of the movement of the watch type terminal 100.

Figure 20A:
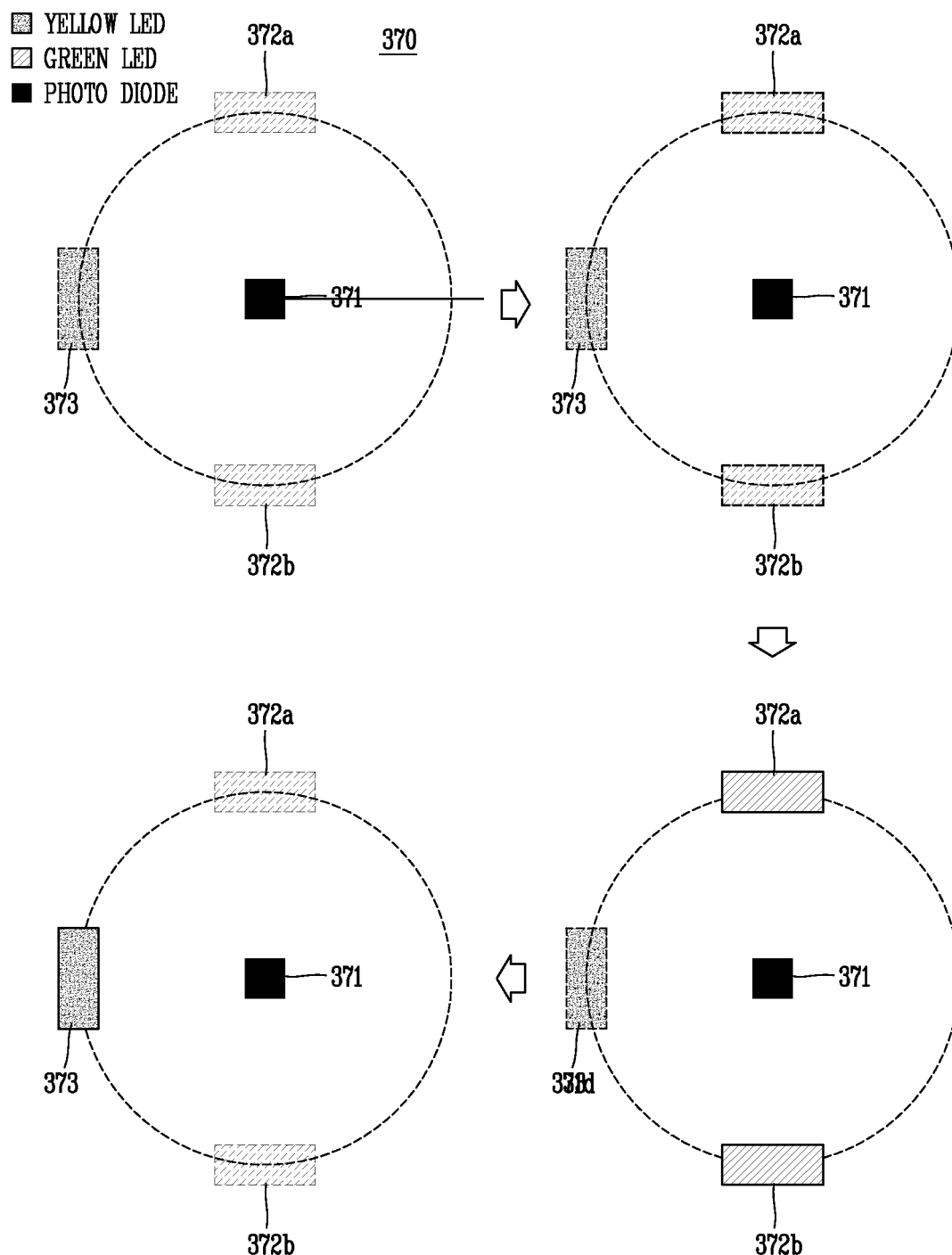
FIGS. 20A and 20B are conceptual views illustrating a control method of adjusting light output according to a depth of a blood vessel.
Figure 20B:
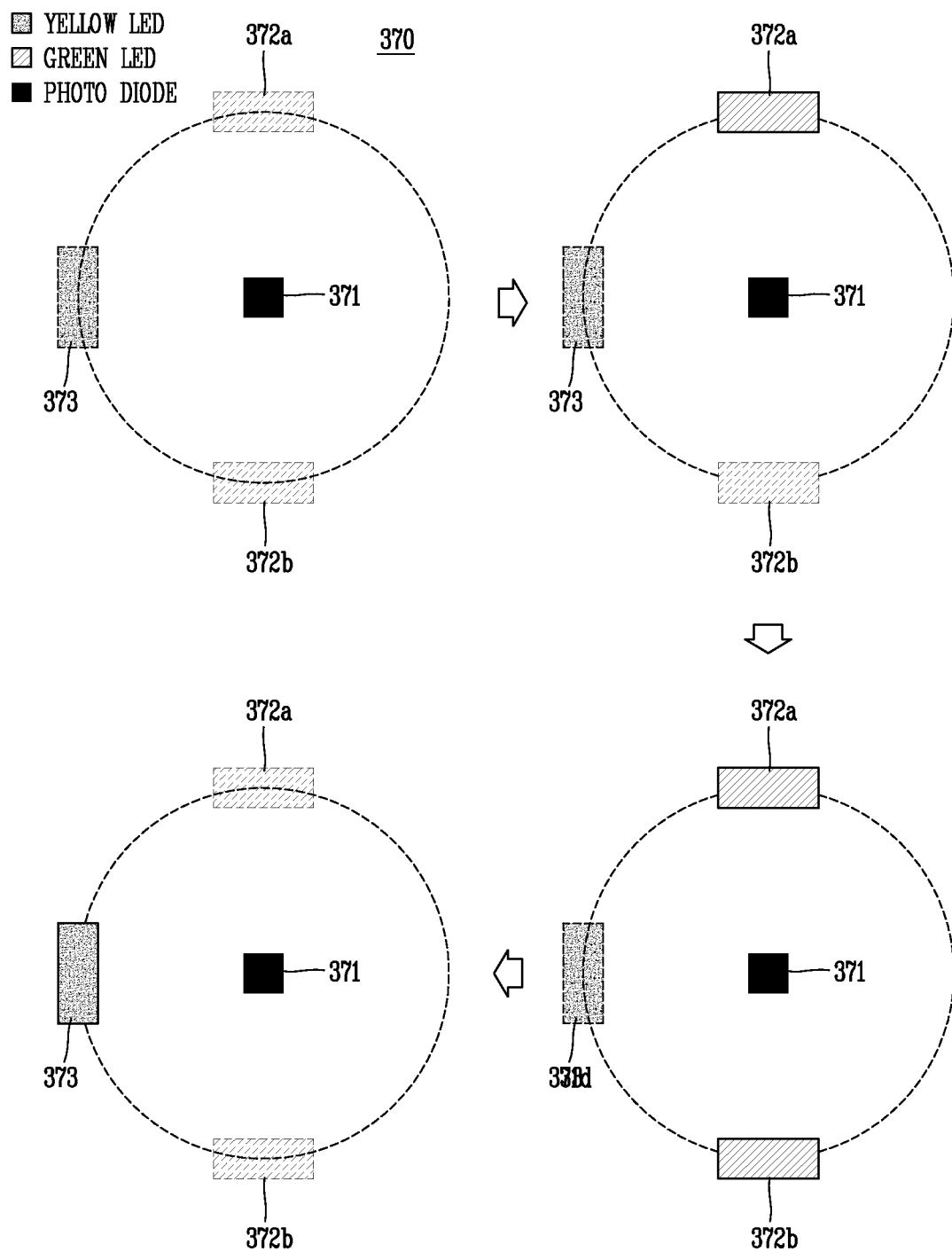

FIGS. 20A and 20B are conceptual views illustrating a control method of adjusting output light according to a depth of a blood vessel.

For example, FIGS. 20A and 20B illustrate a seventh sensing unit 370 including one light receiving sensor 371, first and second green light emitting devices 372a and 372b, and a yellow light emitting device 373.

Referring to FIG. 20A, in an off state of every light emitting device, the controller 180 controls the first and second green light emitting devices 372a and 372b to output a first quantity of green light. When a biometric signal acquired is not in a normal range (i.e., when a pulse is not measured), the controller 180 controls the first and second green light emitting devices 372a and 372b to output a second quantity of green light greater than the first quantity of light.

When the acquired biometric signal is continuously not in the normal range (i.e., when the pulse is not measured), the controller 180 controls the yellow light emitting device 373 to output yellow light. In this instance, the first and second green light emitting devices 372a and 372b are turned off.

Referring to FIG. 20B, the controller 180 activates one green light emitting device and activates two green light emitting devices based on an acquired biometric signal. When the biometric signal within the normal range is not collected continuously, the controller 180 activates the yellow light emitting device 373. In this instance, the first and second green light emitting devices 372a and 372b are turned off.

According to the embodiment, when an accurate measurement is not carried out after an increase in a quantity of light (brightness of light), another type of light appropriate for a skin depth may be output, so as to collect a biometric signal in an optimized state for a user.

The present invention can be implemented as computer-readable codes in a program-recorded medium. The computer-readable medium may include all types of recording devices each storing data readable by a computer system. Examples of such computer-readable media may include hard disk drive (HDD), solid state disk (SSD), silicon disk drive (SDD), ROM, RAM, CD-ROM, magnetic tape, floppy disk, optical data storage element and the like. Also, the computer-readable medium may also be implemented as a format of carrier wave (e.g., transmission via an Internet). The computer may include the controller 180 of the terminal. Therefore, it should also be understood that the above-described embodiments are not limited by any of the details of the foregoing description, unless otherwise specified, but rather should be construed broadly within its scope as defined in the appended claims, and therefore all changes and modifications that fall within the metes and bounds of the claims, or equivalents of such metes and bounds are therefore intended to be embraced by the appended claims.

What is claimed is:

1. A watch type terminal, comprising:
a main body; and
a first sensing unit disposed on one side of the main body and comprising:
   at least one green light emitting device configured to output green light, wherein the at least one green light emitting device comprises four green light emitting devices;
   at least one yellow light emitting device spaced apart from the at least one green light emitting device and configured to output yellow light, a skin transmittance of the yellow light being different from a skin transmittance of the green light; and
   a light receiving sensor surrounded by the at least one green light emitting device and the at least one yellow light emitting device, the light receiving sensor configured to receive light reflected from at least one of the green or yellow light;
a second sensing unit configured to detect a movement of the main body; and
a controller configured to:
   generate a biometric signal based on the reflected light;
   cause each of the four green light emitting devices to output green light one by one in an alternating manner when the movement detected by the second sensing unit is a first level;
   activate two green light emitting devices facing each other, among the four green emitting devices, simultaneously when the movement detected by the second sensing unit is a second level that is higher than the first level; and
   activate all of the four green light emitting devices continuously when the movement detected by the second sensing unit is a third level that is higher than the second level.

2. The terminal of claim 1, wherein the controller is further configured to:
cause the at least one yellow light emitting device to output the yellow light based on the generated biometric signal.

3. The terminal of claim 2, wherein the controller is further configured to:
cause the at least one green light emitting device to output a first quantity of green light; and
cause the at least one green light emitting device to output a second quantity of green light that is greater than the first quantity of green light based on the generated biometric signal.

4. The terminal of claim 3, further comprising a display, wherein the controller is further configured to cause the display to display a guide image for guiding a change of a position of the main body when the biometric signal generated after outputting the yellow light is within an abnormal range.

5. The terminal of claim 1, wherein:
each of the four green light emitting devices is spaced apart from the light receiving sensor by a first length;
the first sensing unit further comprises a red light emitting device spaced apart from the light receiving sensor by a second length that is longer than the first length; and
the red light emitting device is configured to output red light.

6. The terminal of claim 5, wherein the controller is further configured to:
switch the four green light emitting devices into an inactive state when a sleep mode is activated;
activate the red light emitting device to measure and calculate an oxygen saturation value using the red light; and
deactivate the red light emitting device when the sleep mode is inactivated and when at least part of the four green light emitting devices is activated to measure the biometric signal.

7. The terminal of claim 6, wherein the controller is further configured to:
cause the at least one green light emitting device and the at least one yellow light emitting device to be in an inactive state while the red light is output; and
deactivate the red light emitting device while the at least one of the green or yellow light is output.

8. The terminal of claim 6, wherein the at least one green light emitting device and the at least one yellow light emitting device are implemented as an infrared-integrated light emitting diode (IR-integrated LED).

9. The terminal of claim 6, wherein:

the light receiving sensor comprises a first light receiving sensor and a second light receiving sensor; and the first and second light receiving sensors are disposed between the at least one green light emitting device and the at least one yellow light emitting device or disposed to be spaced apart from the at least one green light emitting device based on the at least one yellow light emitting device when the IR sensor, the at least one green light emitting device, the at least one yellow light emitting device, and the red light emitting device are arranged sequentially.

10. The terminal of claim 6, wherein:

the light receiving sensor comprises a first light receiving sensor and a second light receiving sensor;

the IR sensor, the at least one yellow light emitting device, the first and second light receiving sensors, and the red light emitting device are arranged in one direction; and first and second green light emitting devices of the at least one green light emitting device are arranged in a direction intersecting with the one direction.

11. The terminal of claim 1, further comprising:

a display disposed on a front side of the main body; and a rear cover disposed on a back side of the main body, wherein the rear cover comprises:
 a protruding portion protruding from one surface of the rear cover, the sensing unit mounted on the protruding portion; and
 a window coupled to the protruding portion to form an outer surface of the rear cover, the window allowing transmission of light.

12. The terminal of claim 11, wherein:

each of the at least one green light emitting device and the at least one yellow light emitting device is spaced apart from the light receiving sensor by a preset first length on a circuit board;

the window overlaps the circuit board to cover the at least one green light emitting device, the at least one yellow light emitting device, and the light receiving sensor; and the window comprises:
 a transparent area corresponding to the at least one green light emitting device, the at least one yellow light emitting device, and the light receiving sensor; and
 a mask area not allowing transmission of light.

13. The terminal of claim 11, wherein:

each of the at least one green light emitting device and the at least one yellow light emitting device is spaced apart from the light receiving sensor by a preset first length on a circuit board; and at least one opaque light shielding barrier wall is disposed between the at least one green light emitting device and the light receiving sensor and between the at least one yellow light emitting device and the light receiving sensor.

14. The terminal of claim 13, wherein the window is shaped to form a hole in which an end portion of the at least one opaque light shielding barrier wall is inserted.

15. The terminal of claim 13, wherein the at least one opaque light shielding barrier wall surrounds the light receiving sensor and includes an opening through which light is incident onto the light receiving sensor.

16. The terminal of claim 11, further comprising an accommodating unit configured to accommodate the sensing unit therein, wherein the accommodating unit comprises:
 a base portion having a plurality of receiving grooves in which the at least one green light emitting device, the at least one yellow light emitting device, and the light receiving sensor are mounted; and
 a mask portion protruding from the base portion to surround a receiving groove in which the light receiving sensor is received.

17. The terminal of claim 1, wherein:

each of the at least one green light emitting device and the at least one yellow light emitting device is spaced apart from the light receiving sensor by a first length;

the sensing unit further comprises an infrared (IR) sensor; and the IR sensor is spaced apart from the light receiving sensor by a second length that is longer than the first length.

18. The terminal of claim 17, wherein the controller is further configured to detect whether the terminal is worn on a user via the IR sensor.

* * * * *